US008114829B2

(12) United States Patent
Jimenez et al.

(10) Patent No.: US 8,114,829 B2
(45) Date of Patent: Feb. 14, 2012

(54) ELASTIN PROTECTIVE POLYPHENOLICS AND METHODS OF USING THE SAME

(75) Inventors: Felipe Jimenez, San Bernardino, CA (US); Thomas Mitts, Visalia, CA (US); Aleksander Hinek, Toronto (CA)

(73) Assignees: Human Matrix Sciences, LLC, Visalia, CA (US); The Hospital for Sick Children, Toronto, Ontario (CA)

(*) Notice: Subject to any disclaimer, the term of this patent is extended or adjusted under 35 U.S.C. 154(b) by 285 days.

(21) Appl. No.: 12/503,470

(22) Filed: Jul. 15, 2009

(65) Prior Publication Data
US 2010/0016417 A1 Jan. 21, 2010

Related U.S. Application Data

(63) Continuation of application No. 11/394,354, filed on Mar. 29, 2006, now Pat. No. 7,566,693, which is a continuation-in-part of application No. 11/062,377, filed on Feb. 22, 2005, now Pat. No. 7,666,829.

(60) Provisional application No. 60/665,966, filed on Mar. 29, 2005, provisional application No. 60/758,821, filed on Jan. 13, 2006, provisional application No. 60/671,557, filed on Apr. 15, 2005, provisional application No. 60/681,600, filed on May 17, 2005, provisional application No. 60/737,586, filed on Nov. 17, 2005.

(51) Int. Cl.
*C07K 14/00* (2006.01)
(52) U.S. Cl. ............................... 514/1; 530/300
(58) Field of Classification Search ....... 514/1; 530/300
See application file for complete search history.

(56) References Cited

U.S. PATENT DOCUMENTS

| 4,254,105 | A | | 3/1981 | Fukuda |
| 4,259,318 | A | | 3/1981 | Duhe et al. |
| 4,806,344 | A | | 2/1989 | Gaskin |
| 4,938,969 | A | | 7/1990 | Schinitsky et al. |
| 5,006,331 | A | | 4/1991 | Gaskin |
| 5,079,010 | A | | 1/1992 | Natterer |
| 5,087,442 | A | | 2/1992 | Takaichi et al. |
| 5,140,043 | A | | 8/1992 | Darr et al. |
| 5,169,624 | A | * | 12/1992 | Ziegler et al. ............ 424/59 |
| 5,296,500 | A | | 3/1994 | Hillebrand |
| 6,069,129 | A | | 5/2000 | Sandberg et al. |
| 6,117,435 | A | | 9/2000 | Painter et al. |
| 6,232,458 | B1 | | 5/2001 | Weiss et al. |
| 6,475,501 | B1 | | 11/2002 | Kelly et al. |
| 6,506,731 | B1 | | 1/2003 | Sandberg et al. |
| 6,777,389 | B1 | | 8/2004 | Mitts et al. |
| 6,964,954 | B2 | | 11/2005 | Dalko et al. |
| 7,252,834 | B2 | | 8/2007 | Vyavahare et al. |
| 7,560,430 | B2 | | 7/2009 | Mitts et al. |
| 7,566,693 | B2 | | 7/2009 | Jimenez et al. |
| 7,666,829 | B2 | | 2/2010 | Mitts et al. |
| 2002/0028254 | A1 | | 3/2002 | Nonotte et al. |
| 2002/0127256 | A1 | | 9/2002 | Murad |
| 2003/0054021 | A1 | | 3/2003 | Dalko et al. |
| 2003/0069171 | A1 | | 4/2003 | Petito et al. |
| 2003/0166510 | A1 | | 9/2003 | Pickart |
| 2004/0120918 | A1 | | 6/2004 | Lintner et al. |
| 2004/0153145 | A1 | | 8/2004 | Simionescu et al. |
| 2004/0162232 | A1 | | 8/2004 | Mitts et al. |
| 2005/0059599 | A1 | | 3/2005 | Sandberg et al. |
| 2006/0240066 | A1 | | 10/2006 | Vyavahare et al. |
| 2006/0264375 | A1 | | 11/2006 | Jimenez et al. |
| 2008/0050346 | A1 | | 2/2008 | Jimenez et al. |
| 2009/0082280 | A1 | | 3/2009 | Jimenez et al. |
| 2009/0110709 | A1 | | 4/2009 | Mitts et al. |

FOREIGN PATENT DOCUMENTS

| DE | 100 43 466 A1 | 3/2002 |
| EP | 0283349 | 9/1988 |
| EP | 1145709 A1 | 10/2001 |
| EP | 1284133 B1 | 2/2003 |
| FR | 7 302 M | 9/1969 |
| FR | 2768927 A1 | 4/1999 |
| GB | 2 376 886 A | 12/2002 |
| JP | 63313707 A | 12/1988 |
| JP | 5163131 A | 6/1993 |
| JP | 7138142 A | 5/1995 |
| JP | 2001072571 A | 3/2001 |
| JP | 2001328920 A | 11/2001 |
| JP | 2002205913 A | 7/2002 |
| JP | 2003128511 A | 5/2003 |
| JP | 2006160685 | 6/2006 |
| WO | WO 96/19182 A | 6/1996 |
| WO | WO 00/64472 A1 | 11/2000 |
| WO | WO 2004/047620 A2 | 6/2004 |
| WO | WO 2005/118783 A1 | 12/2005 |
| WO | WO 2007/030145 A2 | 3/2007 |

OTHER PUBLICATIONS

Hinek et al., The Elastin Receptor—A Galactoside-Binding Protein, Mar. 25, 1988, Science, 239:1539-1541.

(Continued)

*Primary Examiner* — Karen Carlson
(74) *Attorney, Agent, or Firm* — Pepper Hamilton LLP

(57) ABSTRACT

Dermal fibroblasts permanently loose their ability to synthesize elastin, the major component of elastic fibers, shortly after puberty. This progressive loss of elastic fibers cannot be replaced, resulting in the physical signs of aging. The present invention provides methods and compositions containing the polyphenols ellagic acid and/or tannic acid for protection against degradation of cutaneous elastic fibers by the elastolytic enzymes. The use of ellagic acid and/or tannic acid increased the overall deposition of elastic fibers in healthy and damaged skin cells. The protection of both intra-tropoelastin and extra-cellular mature elastic fibers from proteolytic enzymes by ellagic acid and tannic acid caused an increase in the net deposition of elastic fibers. Therefore, embodiments of the present invention provide methods and composition for the treatment of skin and prevention and treatment of degradation of dermal elastic fibers.

16 Claims, 5 Drawing Sheets
(2 of 5 Drawing Sheet(s) Filed in Color)

OTHER PUBLICATIONS

Hinek, Nature and the Multiple Functions of the 67-kD Elastin-/Laminin Binding Protein, 1994, Cell Adhes. Commun., 2:185-193.

Privitera et al., The 67-kDa Enzymatically Inactive Alternatively Spliced Variant of β-Galactosidase is Identical to the Elastin/Laminin-Binding Protein, Mar. 13, 1998, J. Biol. Chem., 273(11):6319-6326.

Thomas et al. eds., Oxygen Radicals and Disease Process, Harwood Academic Publishers, Newark, NJ 1998 (TOC).

Goldberg et al., Phenolic Constituents, Furans, and Total Antioxidant Status of Distilled Spirits, Sep. 28, 1999, J. Agric. Food Chem., 47:3978-3985.

Whitley et al., Intestinal Epithelial Cell Accumulation of the Cancer Preventive Polyphenol Ellagic Acid-Extensive Binding to Protein and DNA, 2003, Biochem. Pharmacol., 66:907-915.

Cholbi et al., Inhibitory Effects of Phenolic Compounds on $CCl_4$-Induced Microsomal Lipid Peroxidation, 1991, Experientia, 47(2):195-199.

Takagi et al., Inhibitory Effects of Vitamin E and Ellagic Acid on 8-Hydroxydeoxyguanosine Formation in Liver Nuclear DNA of Rats Treated with 2-Nitropropane, 1995, Cancer Lett., 91:139-144.

Kaur et al., Antimutagenic Potential of Ellagic Acid Isolated from Terminalia Arjuna, May 1997, Indian J. Exp. Biol., 35:478-482.

Loarca-Pina et al., Inhibitory Effects of Ellagic Acid on the Direct-Acting Mutagenicity of Aflatoxin $B_1$ in the *Salmonella* Microsuspension Assay, 1998, Mutat. Res., 398:183-187.

De Mejia et al., Antimutagenic Effects of Natural Phenolic Compounds in Beans, 1999, Mutat. Res., 441:1-9.

Halliwell et al., Free Radicals in Biology and Medicine, Clarendon Press, Oxford, UK, p. 285, 1993 (TOC).

Stoner et al., Polyphenols as Cancer Chemopreventive Agents, 1995, J. Cell. Biochem., Suppl. 22:169-180.

Lakovleva et al., The Protective Effect of Ellagic Acid in Experimental Myocarditis, 1998, Eksp. Klin. Farmakol. 61:32-34.

Thresiamma et al., Inhibition of Liver Fibrosis by Ellagic Acid, 1996, Indian J. Physiol. Pharmacol., 40(4):363-366.

Singh et al., Protective Effect of Ellagic Acid on Tert-Butyl-Hydroperoxide Induced Lipid Peroxidation in Isolated Rat Hepatocytes, Sep. 1999, Indian J. Exp. Biol., 37:939-940.

Singh et al., Hepatoprotective Effect of Ellagic Acid Against Carbon Tetrachloride Induced Hepatotoxicity in Rats, Oct. 1999, Indian J. Exp. Biol., 37:1025-1026.

Thresiamma et al., Protective Effect of Curcumin, Ellagic Acid and Bixin on Radiation Induced Toxicity, Sep. 1996, Indian J. Exp. Biol., 34(9):845-847.

Thresiamma et al., Protective Effect of Curcumin, Ellagic Acid and Bixin on Radiation Induced Genotoxicity, 1998, J. Exp. Clin. Cancer Res., 17(4):431-434.

Cozzi et al., Taurine and Ellagic Acid: Two Differently-Acting Natural Antioxidants, 1995, Environ. Mol. Mutag., 26:248-254.

Narayanan et al., p53/p21 (WAF1/CIP1) Expression and Its Possible Role in G1 Arrest and Apoptosis in Ellagic Acid Treated Cancer Cells, 1999, Cancer Lett., 136:215-221.

Zhang et al., Inhibition of Liver Microsomal Cytochrome P450 Activity and Metabolism of the Tobacco-Specific Nitrosamine NNK by Capsaicin and Ellagic Acid, 1993, Anticancer Res., 13(6A):2341-2346.

Boukharta et al., Biodistribution of Ellagic Acid and Dose-Related Inhibition of Lung Tumorigenesis in A/J Mice, 1992, 18(2):181-189.

Barch et al., Ellagic Acid Induces NAD(P)H: Quinone Reductase Through Activation of the Antioxidant Responsive Element of the Rat NAD(P)H: Quinone Reductase Gene, 1994, Carcinogenesis, 15(9):2065-2068.

Khanduja et al., Prevention of N-Nitrosodiethylamine-Induced Lung Tumorigenesis by Ellagic Acid and Quercetin in Mice, 1999, Food Chem. Toxicol., 37:313-318.

Hassoun et al., Modulation of TCDD-Induced Fetotoxicity and Oxidative Stress in Embryonic and Placental Tissues of C57BL/6J Mice by Vitamin E Succinate and Ellagic Acid, 1997, Toxicology, 124:27-37.

Frank et al., Ellagic Acid Protects Rat Embryos in Culture from the Embryotoxic Effects of N-Methyl-N-Nitrosourea, 1992, Teratology, 46(2):109-115.

Frank et al., Ellagic Acid Embryoprotection In Vitro: Distribution and Effects on DNA Adduct Formation, 1993, Teratology, 47(4):275-280.

Gali et al., Inhibition of Tumor Promoter-Induced Ornithine Decarboxylase Activity by Tannic Acid and Other Polyphenols in Mouse Epidermis In Vivo, 1991, Cancer Res., 51(11):2820-2825.

Ihantola-Vormisto et al., Anti-Inflammatory Activity of Extracts from Leaves of *Phyllanthus emblica*, 1997, Planta Medica, 63:518-524.

Stich et al., The Effect of Retinoids, Carotenoids and Phenolics on Chromosomal Instability of Bovine Papillomavirus DNA-Carrying Cells, 1990, Mutat. Res., 241(4):387-393.

Mizuno et al., Inhibitory Effect of Tannic Acid Sulfate and Related Sulfates on Infectivity, Cytopathic Effect, and Giant Cell Formation of Human Immunodeficiency Virus, 1992, Planta Medica, 58(6):535-539.

Akiyama et al., Antibacterial Action of Several Tannins Against *Staphylococcus aureus*, 2001, J. Antimicrob. Chemother., 48(4):487-491.

Kageyama et al., Ultrastructural Visualization of Elastic Fibres with a Tannate-Metal Salt Method, 1985, Histochem. J., 17(1):93-103.

Bellosta et al., Inhibition of Metalloproteinase-9 Activity and Gene Expression by Polyphenolic Compounds Isolated from the Bark of *Tristaniopsis calobuxus* (Myrtaceae), 2003, Cell Mol. Life Sci., 60(7):1440-1448.

Liu et al., Tannic Acid Stimulates Glucose Transport and Inhibits Adipocyte Differentiation in 3T3-L1 Cells, 2005, J. Nutr., 135:165-171.

Roark et al., The Association of Human Fibulin-1 with Elastic Fibers: An Immunohistological, Ultrastructural, and RNA Study, J. Histochem. and Cytochem., vol. 43(4):401-411, 1995.

Gibson et al., Further Characterization of Proteins Associated with Elastic Fiber Microfibrils Including the Molecular Cloning of MAGP-2 (MP25), Jan. 12, 1996, The American Society for Biochemistry and Molecular Biology, Inc., 271(2):1096-1103, Printed May 19, 2005.

Kielty et al., Fibrillin: From Microfibril Assembly to Biomechanical Function, Feb. 28, 2002, Biological Sciences, 357(1418):207-217.

Nakamura et al., Fibulin-5/DANCE is Essential for Elastogenesis In Vivo, Nature 415:171-175, Jan. 10, 2002.

Debelle et al., Elastin: Molecular Description and Function, 1999, Int. J. Biochem. Cell Biol, 31(2):261-272.

Csiszar, Lysyl Oxidases: A Novel Multifunctional Amine Oxidase Family, 2001, Progress in Nucleic Acid Research and Molecular Biology, 70:1-32.

Kielty et al., Elastic Fibres, 2002, Journal of Cell Science, 115:2817-2828.

Parks et al., Developmental Regulation of Tropoelastin Isoforms, Mar. 25, 1988, J. Biol. Chem., 263(9):4416-4423.

Swee et al., Developmental Regulation of Elastin Production: Expression of Tropoelastin Pre-Mrna Persists After Down-Regulation of Steady-State mRNA Levels, Jun. 23, 1995, 270(25):14899-14906.

Ritz-Timme et al., Aspartic Acid Racemization: Evidence for Marked Longevity of Elastin in Human Skin, 2003, Br. J. Dermatol., 149(5):951-959.

Degterev et al., The Role of NF-1 Factors in Regulation of Elastin Gene Transcription, Jun. 1, 1999, Matrix Biology, 18(3):295-307.

Hew et al., Identification of a GA-Rich Sequence as a Protein-Binding Site in the 3'-Untranslated Region of Chicken Elastin mRNA with a Potential Role in the Development Regulation of Elastin mRNA Stability, May 26, 2000, J. Biol. Chem., 275(32):24857-24864.

Kucich et al., Transforming Growth Factor-β Stabilizes Elastin mRNA by a Pathway Requiring Active smads, Protein Kinase C-δ, and p38, Feb. 2002, Am. J. Respir. Cell Mol. Biol., 26(2):183-188.

Li et al., Elastin Point Mutations Cause an Obstructive Vascular Disease, Supravalvular Aortic Stenosis, 1997, Human Molecular Genetics, 6(7):1021-1028.

Francke, Williams-Beuren Syndrome: Genes and Mechanisms, 1999, Human Molecular Genetics, 8(10):1947-1954.

Aessopos et al., Elastic Tissue Abnormalities Resembling Pseudoxanthoma Elasticum in β Thalassemia and the Sickling Syndromes, Jan. 1, 2002, Blood, 99(1):30-35.

Pierce et al., 1,25-Dihydroxyvitamin $D_3$ Represses Tropoelastin Expression by a Posttranscriptional Mechanism, Jun. 5, 1991, J. Biol. Chem., 267(16):11593-11599.

Parks et al., Phorbol Ester-Mediated Downregulation of Tropoelastin Expression is Controlled by a Posttranscriptional Mechanism, 1992, Biochemistry, 31(29):6639-6645.

Kucich et al., Stabilization of Elastin mRNA by TGF-β: Initial Characterization of Signaling Pathway, 1997, Am. J. Respir. Cell Mol. Biol., 17(1):10-16.

McGowan et al., Tumor Necrosis Factor-α Regulation of Glucose Transporter (GLUT1) mRNA Turnover, Jan. 19, 1997, J. Biol. Chem., 272(2):1331-1337.

Czyzk-Krzeska et al., Post-Transcriptional Regulation of Tyrosine Hydroxylase Gene Expression by Oxygen in PC12 Cells, 1997, Kidney Int. 51(2): 585-590.

Amara et al., Defining a Novel cis Element in the 3'-Untranslated Region of Mammalian Ribonucleotide Reductase Component R2 mRNA: Role in Transforming Growth Factor-$β_1$ Induced mRNA Stabilization, 1995, Nucleic Acids Research, 23(9):1461-1467.

Fraga et al., Iron Toxicity and Antioxidant Nutrients, 2002, Toxicology, 180(1):23-32.

Alcantara et al., Regulation of Protein Kinase C (PKC) Expression by Iron: Effect of Different Iron Compounds on PKC-β and PKC-α Gene Expression and Role of the 5'-Flanking Region of the PKC-β Gene in the Response to Ferric Transferrin, 1994, Blood 84(10):3510-3517.

Breuer et al., Dynamics of the Cytosolic Chelatable Iron Pool of K562 Cells, 1996, FEBS Letters, 382(3):304-308.

Brenneisen et al., Central Role of Ferrous/Ferric Iron in the Ultraviolet B Irradiation-Mediated Signaling Pathway Leading to Increased Interstitial Collagenase (Matrix-Degrading Metalloprotease(MMP)-1) and Stromelysin-1 (MMP-3) mRNA Levels in Cultured Human Dermal Fibroblasts, 1998, J. Biol. Chem., 273(9):5279-5287.

Rodems et al., Separate DNA Elements Containing ATF/CREB and IE86 Binding Sites Differentially Regulate the Human Cytomegalovirus UL112-113 Promoter at Early and Late Times in the Infection, 1998, J. Virol., 72(4):2697-2707.

Zhang et al., Transforming Growth Factor-β Reverses a Posttranscriptional Defect in Elastin Synthesis in a Cutis Laxa Skin Fibroblast Strain, Mar. 1995, The Journal of Clinical Investigation, Inc., 95:986-994.

Cazzola et al., Manipulations of Cellular Iron Metabolism for Modulating Normal and Malignant Cell Proliferation: Achievements and Prospects, May 15, 1990, Blood, 75(10):1903-1919.

Richardson et al., The Effect of the Iron (III) Chelator, Desferrioxamine, on Iron and Transferrin Uptake by the Human Malignant Melanoma Cell, Feb. 1, 1994, Cancer Research, 54(3):685-689.

Kicic et al., Effect of Iron Chelators on Proliferation and Iron Uptake in Hepatoma Cells, Dec. 15, 2001, Cancer, 92(12):3093-3110.

Suzuki et al., Oxidants as Stimulators of Signal Transduction, 1997, Free Radical Biology and Medicine, 22(1/2):269-285.

Rothman et al., Cellular Pool of Transient Ferric Iron, Chelatable by Deferoxamine and Distinct from Ferritin, that is Involved in Oxidative Cell Injury, 1992, Molecular Pharmacology, 42(4):703-710.

Konijn et al., The Cellular Labile Iron Pool and Intracellular Ferritin in K562 cells, Sep. 15, 1999, Blood, 94(6):2128-2134.

Verhaegh et al., Regulation of p53 by Metal Ions and by Antioxidants: Dithiocarbamate Down-Regulates p53 DNA-Binding Activity by Increasing the Intracellular Level of Copper, Oct. 1997, Molecular and Cellular Biology, 17(10):5699-5706.

Ye et al., cDNA Cloning by Amplification of Circularized First Strand cDNAs Reveals Non-Ire-Regulated Iron-Responsive mRNAs, 2000, Biochemical and Biophysical Research Communications 275(1):223-227.

Wendler et al., Identification of Pirin, a Novel Highly Conserved Nuclear Protein, Mar. 28, 1997, J. Biol. Chem., 272(13):8482-8489.

Pang et al., Crystal Structure of Human Pirin: An Iron-Binding Nuclear Protein and Transcription Cofactor, Jan. 9, 2004, J. Biol. Chem., 279(2):1491-1498.

Lee et al., Serum Markers of Stored Body Iron are Not Appropriate Markers of Health Effects of Iron: A Focus on Serum Ferritin, 2004, Medical Hypotheses, 62(2):442-445.

Browne et al., The Molecular Pathobiology of Cell Membrane Iron: The Sickle Red Cell as a Model, 1998, Free Radical Biology and Medicine, 24(6):1040-1048.

Frenette, Sickle Cell Vaso-Occlusion: Multistep and Multicellular Paradigm, 2002, Curr Opin. Hematol., 9(2):101-106.

Ilias et al., Loss of ATP-Dependent Transport Activity in Pseudoxanthoma Elasticum-Associated Mutants of Human ABCC6 (MRP6), May 10, 2002, J. Biol. Chem., 277(19):16860-16867.

Beck et al., The Distribution of Abcc6 in Normal Mouse Tissues Suggests Multiple Functions for this ABC Transporter, 2003, The Journal of Histochemistry & Cytochemistry, 51(7):887-902.

Kuroki et al., Reactive Oxygen Intermediates Increase Vascular Endothelial Growth Factor Expression in Vitro and In Vivo, Oct. 1996, J. Clin. Invest., 98(7):1667-1675.

Esposito et al., Redox-Mediated Regulation of $p21^{waf1/cip1}$ Expression Involves a Post-Transcriptional Mechanism and Activation of the Mitogen-Activated Protein Kinase Pathway, 1997, European Journal of Biochemistry, 245:730-737.

Fischer et al., Neutrophil Elastase Induces MUC5AC Gene Expression in Airway Epithelium Via a Pathway Involving Reactive Oxygen Species, 2002, Am. J. Respir. Cell Mol. Biol., 26(4):447-452.

Demple, Grasping the Message: Regulated mRNA Stability in Free Radical Stress Responses, 2004, Redox Report, 9(1):3-5.

Decker et al., A Turnover Pathway for Both Stable and Unstable mRNAs in Yeast: Evidence for a Requirement for Deadenylation, 1993, Genes & Development 7:1632-1643.

Ford et al., The Poly(A) Tail Inhibits the Assembly of a 3'-to-5' Exonuclease in an In Vitro RNA Stability System, Jan. 1997, Molecular and Cellular Biology, 17(1):398-406.

Zaidi et al., Multiple Proteins Interact at a Unique cis-Element in the 3'-Untranslated Region of Amyloid Precursor Protein mRNA, Sep. 30, 1994, Journal of Biological Chemistry, 269(39):24000-24006.

Tinker et al., Tropoelastin Production and Tropoelastin Messenger RNA Activity Relationship to Copper and Elastin Cross-Linking in Chick Aorta, 1986, Biochem. J., 237(1):17-23.

Seyama et al., Effects of Oral Contraceptive Steroids on Aortic Collagen, Elastin and Cholesterol Levels in Iron-Deficient Rats, Jan. 22, 1988, Int. J. Vit. Nut. Res., 58(2):231-235.

Vaxman et al., Can the Wound Healing Process be Improved by Vitamin Supplementation? Experimental Study on Humans, 1996, Eur. Surg. Res., 28(4):306-314.

Senior et al., Val-Gly-Val-Ala-Pro-Gly, A Repeating Peptide in Elastin, Is Chemotactic for Fibroblasts and Monocytes, 1984, J. Cell Biol., 99:870-874.

Senior et al., Chemotactic Responses of Fibroblasts to Tropoelastin and Elastin-Derived Peptides, Sep. 1982, J. Clin. Invest., 70:614-618.

Grosso et al., Peptide Sequences Selected by BA4, a Tropoelastin-Specific Monoclonal Antibody, are Ligands for the 67-kilodalton Bovine Elastin Receptor, 1993, Biochemistry, 32(48):13369-13374.

Morgan et al., Approaches to the Discovery of Non-Peptide Ligands for Peptide Receptors and Peptidases, 1989, Ann. Rep. Med. Chem., 24:243-252.

Ripka et al., Peptidomimetic Design, 1998, Curr. Op. Chem. Biol. 2:441-452.

Hruby et al., Synthesis of Oligopeptide and Peptidomimetic Libraries, 1997, Curr. Op. Chem. Biol., 1:114-119.

Hruby et al., Conformational and Topographical Considerations in Designing Agonist Peptidomimetics from Peptide Leads, 2000, Curr. Med. Chem., 7(9):945-970.

Hinek, Biological Roles of the Non-Integrin Elastin/Laminin Receptor, Jul./Aug. 1996, Biol. Chem., 377:471-480.

Mochizuki et al., Signaling Pathways Transduced Through the Elastin Receptor Facilitate Proliferation of Arterial Smooth Muscle Cells, Nov. 22, 2002, J. Biol. Chem., 277(47):44854-44863.

Brassart et al., Conformational Dependence of Collagenase (Matrix Metalloproteinase-1) Up-Regulation by Elastin Peptides in Cultured Fibroblasts, 2001, J. Biol. Chem., 276(7):5222-5227.

Huet et al., [Effect of Elastin Peptides on the Production of Matrix Metalloproteinase 2 by Human Skin Fibroblasts in Culture], 2001, J. Soc. Biol., 195(2):165-172 (abstract).

Priyadarsini et al., Free Radical Studies of Ellagic Acid, a Natural Phenolic Antioxidant, Feb. 26, 2002, J. Agric. Food Chem., 50(7):2200-2206.

deAncos et al., Ellagic Acid, Vitamin C, and Total Phenolic Contents and Radical Scavenging Capacity Affected by Freezing and Frozen Storage in Raspberry Fruit, Sep. 19, 2000, J. Agric. Food Chem., 48(10):4565-4570.

Bunda et al., Fluctuations of Intracellular Iron Modulate Elastin Production, Jan. 21, 2005, J. Biol. Chem., 280(3):2341-2351.

Devi et al., In Vitro Effects of Natural Plant Polyphenols on the Proliferation of Normal and Abnormal Human Lymphocytes and Their Secretions of Interleukin-2, 1993, Cancer Lett., 69:191-196.

Hinek et al., Impaired Elastic-Fiber Assembly by Fibroblasts from Patients with Either Morquio B Disease or Infantile GM1-Gangliosidosis is Linked to Deficiency in the 67-kD Spliced Variant of β-Galactosidase, 2006, Am. J. Hum. Genet., 67:23-36.

Hinek et al., Decreased Elastin Deposition and High Proliferation of Fibroblasts from Costello Syndrome are Related to Functional Deficiency in the 67-kD Elastin-Binding Protein, 2000, Am. J. Hum. Genet., 66:859-872.

Hinek et al., Impaired Elastogenesis in Hurler Disease: Dermatan Sulfate Accumulation Linked to Deficiency in Elastin-Binding Protein and Elastic Fiber Assembly, Mar. 2000, Am. J. Pathol., 156(3):925-938.

Urban et al., Connection Between Elastin Haploinsufficiency and Increased Cell Proliferation in Patients with Supravalvular Aortic Stenosis and Wiliams-Beuren Syndrome, 2002, Am. J. Hum. Genet. 71:30-44.

Hinek et al., 67-kD Elastin-Binding Protein is a Protective "Companion" of Extracellular Insoluble Elastin and Intracellular Tropoelastin, 1994, J. Cell. Biol. 126(2):563-574.

Hinek et al., Heterotopic Allotransplantation of Isolated Aortic Cells. An Electron Microscopic Study, 1976, Cell Tissue Res. 172:59-79.

Hinek et al., Electron Microscopic Observations on the Formation of Elastic Fibers in Primary Cultures of Aortic Smooth Muscle Cells, 1977, J. Ultrastruct. Res. 60:12-20.

Hinek et al., Elastin Formation in Heterotopic Transplants of Isolated Arterial Smooth Muscle Cells, 1981, Elastin Formation in Heterotopic Transplants of Isolated Arterial Smooth Muscle Cells, 1981, Connect Tissue Res. 8:181-184.

Isenburg et al., Elastin Stabilization in Cardiovascular Implants: Improved Resistance to Enzymatic Degradation by Treatment with Tannic Acid, 2004, Biomaterials 25:3293-3302.

Isenburg et al., Tannic Acid Treatment Enhances Biostability and Reduces Calcification of Glutaraldehyde Fixed Aortic Wall, 2005, Biomaterials 26:1237-1245.

Bock et al., Activation of Intrinsic Blood Coagulation by Ellagic Acid: Insoluble Ellagic Acid-Metal Ion Complexes are the Activating Species, 1981, Biochemistry 20:7258-7266.

Chino et al., Effects of DA-9065a, an Inhibitor of Factor Xa, on Ellagic Acid-Induced Plantar Skin Thrombosis Assessed in Tetrodotoxin-and $N^{\omega}$-Nitro-L-Arginine-Treated Rats, 2003, J. Pharmacol. Sci. 91:319-329.

Hara et al., Preventive Effect of Argatroban on Ellagic Acid-Induced Cerebral Thromboembolism in Rats, 1994, Haemostasis 24:351-357.

Uzunova et al., Gonadal Hormones and Pathogenesis of Occlusive Arterial Thrombosis, 1978, Am. J. Physiol. 234(4):H454-459.

Arribas et al., Elastic Fibres and Vascular Structure in Hypertension, 2006, Pharm. & Therapeutics, Feb. 20, 2006, pp. 1-21.

Banda et al., Mouse Macrophage Elastase. Purification and Characterization as a Metalloproteinase, 1981, Biochem. J. 193:589-605.

Gori et al., [Tannin and Gallic Acid as Marker of Exposure to Hardwood Dust], 2005, G. Ital. Med. Lav. Ergon 27(3):332-334 (abstract).

Hinek et al., Proteolytic Digest Derived from Bovine Ligamentum Nuchae Stimulates Deposition of New Elastin-Enriched Matrix in Cultures and Transplants of Human Dermal Fibroblasts, 2005, J. Dermatol. Sci. 39:155-166.

Ignatowicz et al., The Effect of Plant Phenolics on the Formation of 7,12-Dimethylbenz[a]anthracene-DNA Adducts and TPA-Stimulated Polymorphonuclear Neutrophils Chemiluminescence In Vitro, 2003, Toxicology 189:199-209.

Losso et al., In Vitro-Anti-Proliferative Activities of Ellagic Acid, 2004, J. Nutr. Biochem. 15:672-678.

Mecham et al., Elastin Degradation by Matrix Metalloproteinases. Cleavage Site Specificity and Mechanisms of Elastolysis, 1997, J. Biol. Chem. 272(29):18071-18076.

Miao et al., Sequence and Structure Determinants for the Self-Aggregation of Recombinant Polypeptides Modeled After Human Elastin, 2003, J. Biol. Chem. 278(29):48553-48562.

Mrowietz et al., Selective Inactivation of Human Neutrophil Elastase by Synthetic Tannin, 1991, J. Invest. Dermatol. 97(3):529-533.

Nam et al., Tannic Acid Potently Inhibits Tumor Cell Proteasome Activity, Increases p27 and Bax Expression, and Induces G1 Arrest and Apoptosis, 2001, Cancer Epidemiol. Biomarkers & Prev. 10:1083-1088.

Ramanathan et al., Cytotoxic Effect of Plant Polyphenols and Fat-Soluble Vitamins on Malignant Human Cultured Cells, 1992, Cancer Lett. 62:217-224.

Starcher et al., Antibody Raised to AKAAAKAAAKA Sequence on Tropoelastin Recognizes Tropoelastin but Not Mature Crosslinked Elastin: A New Tool in Metabolic and Structural Studies of Elastogenesis, 1999, Connect Tissue Res. 40(4):273-282.

Taitzoglou et al., Dietary Administration of Tannic Acid Lowers Plasminogen Activator in the Liver of C3H Hepatoma Bearing Male Mice, 2000, In Vivo 14:767-771.

Taitzoglou et al., Inhibition of Human and Ovine Acrosomal Enzymes by Tannic Acid in Vitro, 2001, Reproduction 121:131-137.

Tanimura et al., Suppression of Tumor Cell Invasiveness by Hydrolyzable Tannins (Plant Polyphenols) Via the Inhibition of Matrix Metalloproteinase-2/-9 Activity, 2005, Biochem. & Biophys. Res. Commun. 330:1306-1313.

Vayalil et al., Proanthocyanidins from Grape Seeds Inhibit Expression of Matrix Metalloproteinases in Human Prostate Carcinoma Cells, Which is Associated with the Inhibition of Activation of MAPK and NFκB, 2004, Carcinogenesis 25(6):987-995.

Tajima et al., Modulation by elastin peptide VGVAPG of cell proliferation and elastin expression in human skin fibroblasts, 1997, Arch. Dermatol. Res. 289:489-492.

Lowe et al. eds., Sunscreens: Development, Evaluation, and Regulatory Aspects 2nd ed., Marcel Dekker, Inc., New York, New York, 1997, p. 229.

European Supplementary Search Report dated May 21, 2010 for EP 06824685.

International Search Report dated Feb. 6, 2008 for PCT/US2006/012027.

Moroy et al. "Structural Characterization of Human Elastin Derived Peptides Containing the GXXP Sequence" Nov. 2005, *Biopolymers* 78:206-220.

\* cited by examiner

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Val Gly Ala Met Pro Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Val Gly Leu Met Pro Gly
1               5

<210> SEQ ID NO 3
<211> LENGTH: 6
<212> TYPE: PRT
<213> ORGANISM: Artificial Sequence
```

```
<220> FEATURE:
<223> OTHER INFORMATION: Synthetic peptide

<400> SEQUENCE: 3

Val Gly Val Met Pro Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Val Gly Ala Ser Pro Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Val Gly Ala Ala Pro Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Val Gly Leu Ser Pro Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Val Gly Leu Ala Pro Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Val Gly Val Ser Pro Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 9

Ile Gly Ala Met Pro Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Ile Gly Leu Met Pro Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Ile Gly Val Met Pro Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Ile Gly Ala Ser Pro Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Ile Gly Ala Ala Pro Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Ile Gly Leu Ser Pro Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15
```

```
Ile Gly Leu Ala Pro Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Ile Gly Val Ser Pro Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Ile Gly Val Ala Pro Gly
1               5
```

ELASTIN PROTECTIVE POLYPHENOLICS AND METHODS OF USING THE SAME

CROSS REFERENCE TO RELATED APPLICATIONS

This application is a continuation of U.S. patent application Ser. No. 11/394,354 filed Mar. 29, 2006, which is a nonprovisional of and claims priority to U.S. Provisional Patent Application No. 60/665,966 filed Mar. 29, 2005, U.S. Provisional Patent Application No. 60/758,821 filed Jan. 13, 2006, U.S. Provisional Patent Application No. 60/681,600 filed May 17, 2005, U.S. Provisional Patent Application No. 60/671,557 filed Apr. 15, 2005 and U.S. Provisional Patent Application No. 60/737,586 filed Nov. 17, 2005, and is a continuation-in-part of and claims priority to U.S. patent application Ser. No. 11/062,377 filed Feb. 22, 2005, the disclosures of which are incorporated herein by reference in their entirety.

STATEMENT REGARDING FEDERALLY SPONSORED RESEARCH PROJECTS

Not Applicable

NAMES OF PARTIES SUBJECT TO A JOINT RESEARCH AGREEMENT

Not Applicable

INCORPORATION BY REFERENCE OF MATERIAL SUBMITTED ON A DISC

Not Applicable

BACKGROUND

Children with inherited diseases, characterized by impaired primary deposition of elastic fibers (i.e. Costello Syndrome or Cutis Laxa) develop wrinkles and deep dermal creases. Similar, but steadily developing signs of premature skin aging can also be observed in individuals with Pseudoxanthoma Elasticum and in normal persons after prolonged exposure to sun. Histological analysis of wrinkled skin demonstrates disappearance and altered organization of elastic fibers due to premature proteolytic degradation and impaired remodeling (solar elastosis) of these components of dermal extracellular matrix. This observed loss of physiologically relevant elastic fibers is also affected by the fact that fully differentiated (adult) dermal fibroblasts lose their ability to synthesize elastin and thus cannot replace damaged elastic fibers. Since elastic fibers are solely responsible for cutaneous elasticity/resilience there is an obvious need for development of methods that might protect existing elastic fibers from premature degradation by elastolytic proteinases and facilitate new elastogenesis in skin.

A proteolytic digest of elastin to provide a mixture of small elastin-derived peptides (ProK-60), manganese salts ($MnCl_2$, $MnSO_4$ and MnPCA) and trivalent iron (Ferric Ammonium Citrate) have each been shown to individually stimulate the production and effective assembly of new tropoelastin into new elastic fibers in both primary cultures of human dermal fibroblasts and in organ cultures of human adult skin explants. Yet even under optimal conditions, the elastogenic process is not 100% efficient. A significant fraction (30-40%) of newly produced tropoelastin is not assembled into extracellular elastic fibers. Instead, these unassembled tropoelastin interact with the cell surface elastin receptor and further stimulate new elastogenesis, pro-mitogenic signaling pathways and pro-migratory signaling pathways. Moreover, these unassembled tropoelastin molecules and the soluble products of proteolytic degradation of insoluble elastin can stimulate the secretion of elastolytic metalloproteinases. While stimulation of dermal fibroblast proliferation and migration can contribute to the overall anti-aging effect induced by factors initially triggering new elastogenesis, the simultaneous up-regulation of elastolytic enzymes may cause rapid degradation of newly produced elastin and existing elastic fibers. Hence there is a need to protect existing and new elastic fibers from premature enzymatic proteolysis.

It has now been shown that the treatment of cultured dermal fibroblasts with ellagic acid or tannic acid significantly enhances their net deposition of elastic fibers. This effect is due to the fact that these reagents bind to the newly produced elastin and protect it from proteolytic degradation.

Ellagic acid and tannic acid are polyphenols found in a wide variety of fruits and nuts such as raspberries, strawberries, walnuts, grapes, and black currants. These molecules possess potent ability to scavenge reactive oxygen species (ROS) and reactive nitrogen species (RNS). Both ROS and RNS, generated inside cells after exposure to several endogenous and exogenous agents, may cause direct or indirect damage of many important biomolecules, including elastin mRNA, by activation of local proteinases, glycosidases or RNAses. Moreover, tannic acid has been shown to bind to insoluble bovine and porcine elastin and inhibit their degradation by porcine pancreatic elastase and recently, ellagic acid was shown to decrease expression of pro-MMP-2 and pro-MMP-9, precursors of two elastolytic enzymes.

The most extensively studied polyphenol, ellagic acid, exhibits minimal solubility in water and moderate to better solubility in organic solvents such as methanol and DMSO, suggesting that ellagic acid may act as a good lipophilic antioxidant. Experimental data indicate that ellagic acid inhibits lipid peroxidation at much lower concentrations than vitamin E. This property, along with its ability to scavenge peroxyl radicals, makes it a probable chain-breaking antioxidant candidate.

Epidemiological studies indicate that there is an inverse association between the incidence of coronary heart diseases and fruit consumption, largely attributed to the antioxidant nature of phenolic compounds. Ellagic acid exhibits cardio-protective properties in the neoepinephrine myocarditis rat model, hepato-protective activity against carbon tetrachloride both in vitro and in vivo and reduced cytogenetic damage induced by radiation, hydrogen peroxide and mitomycin C.

Additional experimental studies have demonstrated that ellagic acid, tannic acid and their derivatives, due to their planar structure, also bind to DNA by intercalating into the minor groove and exhibit anti-mutagenic, anti-cancer and anti-proliferative activities. In addition, ellagic acid induces G1 arrest and inhibits overall cell growth, causing apoptosis in several tumor cells. Ellagic acid has also been shown to inhibit chemically induced cancer in the lung, liver, skin and esophagus of rodents, including TPA-induced tumor promotion in mouse skin. Given the common etiopathogenic processes of mutagenesis, carcinogenesis, and teratogenesis induced by genotoxic chemicals, ellagic acid was also tested for embryoprotection and demonstrated that it can interrupt the critical teratogenic events induced by methylating agents.

Topical applications of ellagic acid have been used in therapeutic preparations. Gali, et. al. demonstrated that topical applications of tannic acid practically inhibit tumor promoter-induced ornithine decarboxylase activity (ODA) in mouse epidermis in vivo suggesting that tannic acid and other polyphenols may be effective not only against skin tumor initiation and complete carcinogenesis, but also against the promotion phase of skin tumorigenesis. Moreover, tannic acid and its polyphenol derivatives have been shown to possess anti-inflammatory activities and to decrease infectivity of human cells with papiloma virus, human immunodeficiency virus, and *Staphylococcus aureus*.

BRIEF SUMMARY OF THE INVENTION

The present invention provides evidence that the effectiveness of ellagic acid or tannic acid to prevent premature proteolytic degradation of tropoelastin and fully polymerized elastin, thus facilitating more efficient elastogenesis. Thus, embodiments of the present invention provide compositions and methods for treating aging or damaged skin using ellagic acid, tannic acid, or derivatives thereof.

BRIEF DESCRIPTION OF THE FIGURES

The file of this patent contains at least one drawing executed in color. Copies of this patent with color drawing(s) will be provided by the Patent and Trademark Office upon request and payment of necessary fee.

DETAILED DESCRIPTION OF THE INVENTION

Figure 1:
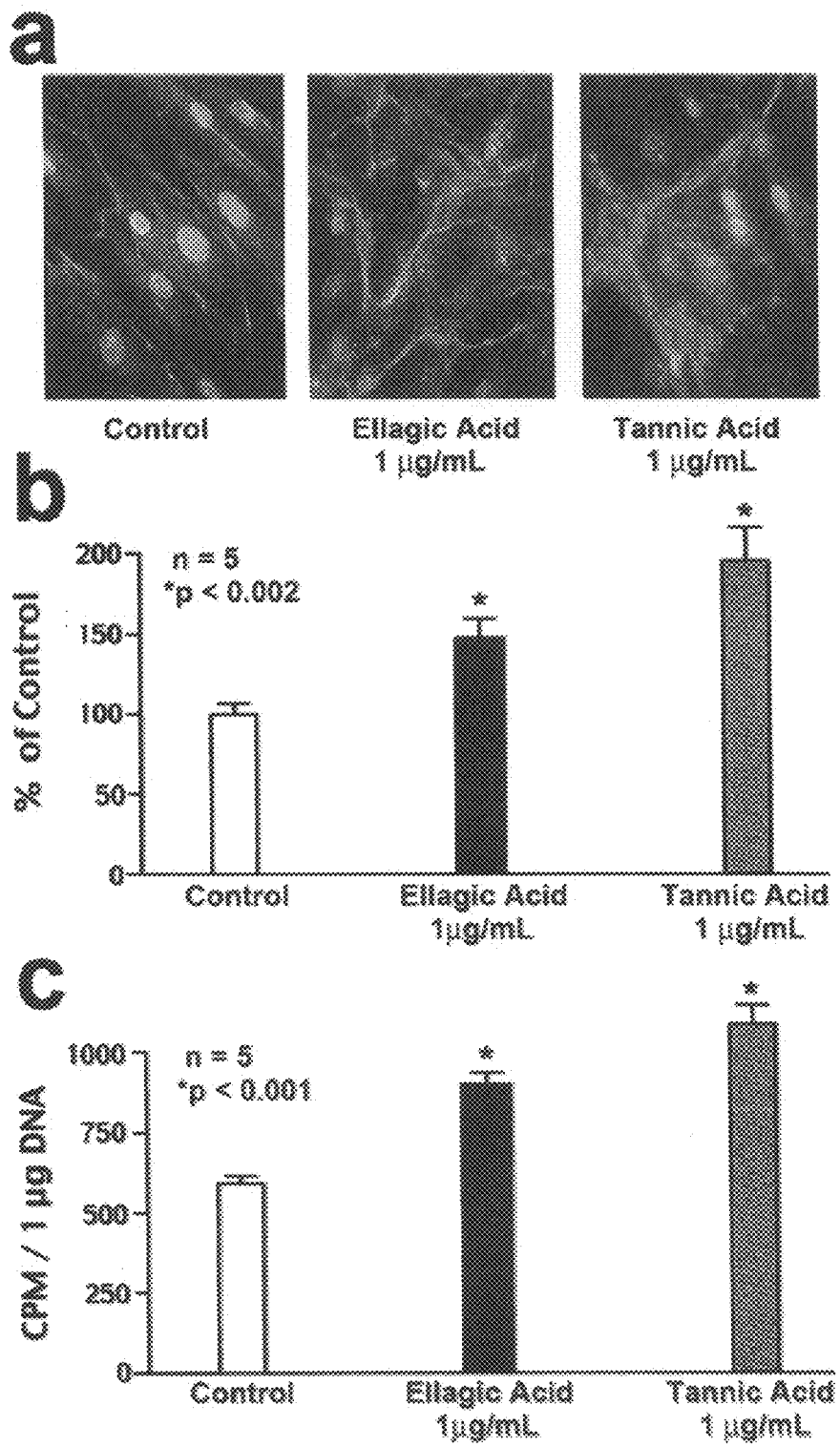
FIG. 1. Assessment of immunodetected and insoluble elastic fibers in dermal fibroblast cultures. (a) Micrographs of immunodetected tropoelastin in cultures maintained in the presence and absence of EA and TA (1 μg/mL each). (b) Results of morphometric evaluation of tropoelastin levels in fibroblast cultures. (c) Evaluation of metabolically labeled insoluble elastin in treated and control cultures. All results were obtained in 7 day-old cultures of dermal fibroblasts derived from a 36 year-old caucasian female. Data demonstrate that treatment with ellagic acid or tannic acid significantly increases a net deposition of extracellular elastic fibers as compared to respective untreated controls.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%. Generally speaking, the term "tissue" refers to any aggregation of similarly specialized cells which are united in the performance of a particular function.

The term "cosmetic," as used herein, refers to a beautifying substance or preparation which preserves, restores, bestows, simulates, or enhances the appearance of bodily beauty or appears to enhance the beauty or youthfulness, specifically as it relates to the appearance of tissue or skin.

The term "modify" is used to convey that the present invention changes either the appearance, form, characteristics and/or the physical attributes of the tissue to which it is being provided, applied or administered. The change in form may be demonstrated by any of the following alone or in combination: enhanced appearance of the skin; increased softness of the skin; increased turgor of the skin; increased texture of the skin; increased elasticity of the skin; decreased wrinkle formation and increased endogenous elastin production in the skin, increased firmness and resiliency of the skin.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, the therapeutic composition is not immunogenic when administered to a human patient for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with a polyphenolic compound, can include, but is not limited to, providing an polyphenolic compound into or onto the target tissue; providing a polyphenolic compound systemically to a patient by, e.g., intravenous injection whereby the therapeutic reaches the target tissue; and the like.

The term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to improve the functionality, the appearance, the elasticity, and/or the elastin content of mammalian tissue. As it applies to skin, it is measured by turgor, tone, appearance, degree of wrinkles, and youthfulness. As the term applies to blood vessels it may be measured by the degree of elasticity or proper vasomotor response (vasodilatation/vasoconstriction) of the vessel. Accordingly, therapeutic treatment of blood vessels may have implications in diseases associated with visco-elasticity, including hypertension, arteriosclerosis, angina, angiogenesis, myocardial infarction, coronary thrombosis, restenosis post angioplasty, and chronic obstructive pulmonary disease.

The terms "therapeutically effective" or "effective", as used herein, may be used interchangeably and refer to an amount of a therapeutic composition of the present invention—e.g., a polyphenolic compound. For example, a therapeutically effective amount of a composition comprising polyphenolic compound is a predetermined amount calculated to achieve the desired effect, i.e., to effectively promote elastin production, cell proliferation, or improved appearance, or improved tissue elasticity in an individual to whom the composition is administered.

As used herein, "tissue", unless otherwise indicated, refers to tissue which includes Elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity.

Skin is composed of a top layer, the epidermis, which is approximately 20 cell layers or about 0.1 mm in thickness, and a lower layer, the dermis, which is from about 1 to about 4 mm in thickness and contains small blood vessels, collagen, elastin and fibroblasts. The dermis provides structural support and nutrients to the epidermis. Aging has been shown to increase cellular heterogeneity of the epidermal layer, however, it has little effect on the thickness of the epidermal layer. The supporting dermis, on the other hand, is known to thin with age and exposure to the sun and environmental contaminants (other environmental effects on the skin are discussed in U.S. Pat. No. 4,938,969 and U.S. Pat. No. 5,140,043, the disclosure of which is herein incorporated by reference). As the dermal layer provides the support and blood supply for the epidermis, the dermal layer is important in maintaining the elasticity and appearance of the skin. Disruption of the supporting dermis leads directly to sagging and, consequently, furrowing of the epidermis, i.e., the formation of wrinkles.

Deep wrinkles are also due to continual stretching and contraction of both the dermis and epidermis. Currently, these deep wrinkles or furrows may only be eliminated by plastic surgery or by collagen injections directly beneath the depressed areas. The fine wrinkles that occur with age and prolonged exposure to the sun and other environmental contaminants are the direct result of deterioration of the supporting dermal layer.

Elastin is secreted by the fibroblasts of the connective tissues and by the vascular smooth muscle cells (i.e., arteries, veins and heart) and elastic cartilage chondrocytes (i.e., epiglottis and ear cartilage) into the extracellular matrix. In the dermal connective tissue, the elastin fibers are thin and sinuous. Elastin contained in the dermis represents 5% of its dry weight. Elastin is a large fibrous protein which is formed by spiral filaments that can be compared to springs. The spiral filaments consist of peptidic chains that can stretch out. The peptidic chains are connected to each other by very specific amino-acids: desmosin and isodesmosin, which builds between them, giving the molecule a reticular aspect. After stretching out, the molecules resume their original shape due to this cross linking, which is essential to molecular elasticity.

The biosynthesis of elastin begins with the embryonic period and continues through adulthood, at which time our body stops producing elastin. Thus, elastin is no longer renewed. With aging, the elastic fibers progressively degenerate and separate into fragments. The skin progressively loses its elasticity, resulting in fine lines and wrinkles. This damage to our elastic tissue cannot be avoided and is part of the natural (physiological) aging process. This process begins relatively early, but accelerates considerably after age 40.

Elastin owes its properties to its thin structure which resembles that of rubber. Elastin is the protein responsible for our skin's essential elasticity and tonicity. Its decrease means the skin starts sagging, allowing fine lines, folds and wrinkles to appear and grow.

One embodiment of the present invention provides compositions comprising at least one polyphenolic compound, or derivatives thereof, preferably ellagic acid or tannic acid or a combination thereof. The polyphenolic compound may be present in an effective amount, for example, to stimulate elastogenesis or protect elastin fibers from degradation. In one embodiment, an effective amount is from about 0.01 µg to about 100 µg, preferably from about 1 µg to about 10 µg.

Compositions of the present invention may further include a stimulator of elastogenesis. Such stimulators of elastogenensis include, but are not limited to, elastin derived peptides, plant derived peptides, bovine derived peptides, manganese, iron, copper and combinations thereof.

Embodiments of the present invention may further comprise an agent selected from anti-inflammatory agents, sunscreens, sunblocks, stimulators of protein synthesis, cell membrane stabilizing agents, moisturizing agents, coloring agents, opacifying agents and combinations thereof.

A further embodiment of the present invention provides compositions comprising at least one polyphenolic compound, or derivatives thereof, preferably ellagic acid or tannic acid and optionally one stimulator of elastogenesis. A stimulator of elastogenesis may be, for example, small elastin-derived peptides including, but not limited to, ProK-60 or other small elastin-derived peptides as set forth in co-pending U.S. application Ser. No. 10/778,253 entitled "Elastin Digest Compositions and Methods Utilizing the Same" filed Feb. 13, 2004, the contents of which are herein incorporated by reference in its entirety. Such compositions may be useful to significantly increase the net deposition of insoluble elastic fibers, thereby enhancing the skin's elasticity and decreasing the appearance of fine lines and/or wrinkles. Thus, further embodiments of the present invention provide compositions and methods to compensate for the loss of elastic components in the dermis.

The result of aging on skin, whether or not it has been accelerated by environmental damage (such as radiation, pollution) is a deterioration of the dermal layer—fewer fibroblasts, less collagen, less elastin and less circulatory support. Consequently, the normal stretching and contraction of the skin leads to damage of the dermis that is not readily corrected, resulting in wrinkling. Further embodiments of the present invention provide methods and compositions for increasing the deposition of insoluble elastin fibers, therein reducing the effects of radiation, including, but not limited to, ultraviolet radiation, or other environmental damage.

Dermatologists and cosmetologists have directed their efforts to improving the appearance of skin using agents known to stimulate the growth and proliferation of epidermal cells. Newly proliferated cells provide more structure and hold more moisture, giving the skin a younger appearance. One method of causing new skin cell proliferation is accomplished by use of an irritant or chemical peel in which the uppermost layers of the epidermis are caused to slough off, leading to proliferation and replacement with new epidermal cells. While such treatment is recognized to provide some cosmetic improvement, it does not address the major causative factor—the compromised supporting dermal layer. Thus, embodiments of the present invention also provide methods and compositions for the enhanced deposition of insoluble elastin fibers, therein providing the dermal support and elasticity necessary for smooth, supple skin.

One embodiment of the invention is a stable, effective topical composition comprising at least one polyphenolic compound, or derivative thereof. Preferably, the polyphenolic compound is selected from tannic acid, ellagic acid, derivatives thereof, salts thereof and combinations thereof.

Another embodiment of the present invention is a method of treating damage to skin, such as often arises due ultraviolet light exposure and/or aging. The method includes applying the present topical composition to a damaged portion of the skin, for example, but not limited to, topically applying compositions of the present invention to the locus of wrinkles. These topical polyphenolic based compositions are particularly effective for reducing epidermal wrinkling resulting from intrinsic aging, photo damage, or other environmental damage.

Such compositions may also be used prophylactically to reduce photo-induced damage which can result from exposure of skin to sunlight and other harmful irradiation.

Another embodiment of the invention is a method of prophylactically applying the compositions of the invention for the protection of the skin against damage which may occur due to radiation or other environmental insults/exposure.

A further embodiment provides a method for treating and/or reducing wrinkles and/or fine lines by contacting skin with a composition of the present invention.

Another embodiment of the invention is a method for stabilizing insoluble elastin fibers present in the skin by contacting the skin with a topical composition of the invention. An object of the present invention is to provide a composition useful in minimizing early and acute ultraviolet radiation damage, as well as late and chronic radiation induced photo damage which together may enhance or cause photoaging of the skin.

It is yet a further object of the present invention to provide in the form of a topical carrier, at least one polyphenolic compound, or derivative thereof, including, but not limited to, tannic acid and/or ellagic acid, which is effective in increasing the amount of insoluble elastin deposition, therein restoring that elastin which is degraded upon exposure to free radicals.

It is another object of the present invention to provide factors, including but not limited to, a source of small elastin-derived peptides (for example, ProK-60), a manganese component (for example, Mn-PCA, manganese sulfate, manganese gluconate), an iron component (for example, ferric ammonium citrate), a copper component (for example, copper-PCA, copper sulfate), bovine-derived peptides or plant-derived peptides to promote elastogenesis for skin repair and wound healing that occurs due to photoaging processes in the skin, such as those that can occur from acute sunburn and/or chronic exposure to ultraviolet radiation. Suitable manganese and iron components are described in co-pending U.S. application Ser. No. 11/062,377 entitled "Compositions for Elastogenesis and Connective Tissue Treatment" filed Feb. 22, 2005, suitable plant-derived peptides are described in co-pending U.S. Application No. 60/671,557 entitled "Plant-Derived Elastin Binding Protein Ligands and Methods of Using the Same" filed Apr. 15, 2005, and suitable bovine-derived peptides are described in co-pending U.S. Application No. 60/681,600 entitled "Proteolytic Digest Derived from Bovine Ligamentum Nuchae Stimulates Deposition of New Elastin-Enriched Matrix in Cultures and Transplants of Human Dermal Fibroblasts" filed May 17, 2005, the contents of which are all herein incorporated by reference in their entireties.

A further embodiment of the present invention provides a composition comprising an effective amount of a polyphenolic compound and an elastin derived peptide is provided. The polyphenolic compound may be selected from tannic acid, ellagic acid and combinations thereof. An effective amount of the polyphenolic compound is preferably from about 1 µg to about 10 µg. In a preferred embodiment, the elastin derived peptide is selected from ProK60, E91 and a combination thereof.

In a further embodiment of the present invention a composition comprising an effective amount of a polyphenolic compound and an elastogenic plant-derived peptide is provided. The polyphenolic compound may be selected from tannic acid, ellagic acid and a combination thereof. An effective amount of the polyphenolic compound is preferably from about 1 µg to about 10 µg.

Another embodiment is a method for protecting elastin fibers from degradation comprising administering an effective amount of a polyphenolic compound to a subject in need thereof. The polyphenolic compound is selected from tannic acid, ellagic acid and a combination thereof. An effective amount of the polyphenolic compound is preferably from about 1 µg to about 10 µg.

In another embodiment, the method may further comprise administering a stimulator of elastogenesis selected from elastin-derived peptides, plant-derived peptides, bovine-derived peptides, manganese, iron, copper and combinations thereof. The polyphenolic compound and the stimulator of elastogenesis may be administered simultaneously or sequentially.

The preparation of a pharmacological composition that contains active ingredients dispersed therein is well understood in the art. Typically such compositions if desired, may be prepared as sterile compositions either as liquid solutions or suspensions, aqueous or non-aqueous, however, suspensions in liquid prior to use can also be prepared.

The active ingredient of the present invention may be mixed with excipients which are pharmaceutically acceptable and compatible with the active ingredient and in amounts suitable for use in the therapeutic methods described herein. Various excipients may be used as carriers for the peptide compositions of the present invention as would be known to those skilled in the art. For example, compounds may be dissolved excipients such as water comprising solutions, alcohol comprising mixtures, intravenous and saline comprising mixture, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

Formulations comprising polyphenolics, for example ellagic acid or tannic acid, may be prepared by mixing such excipients with the polyphenolic. The polyphenolic compounds in the formulation may comprise from about 0.0002 to about 90% by weight of the formulation. These formulations may be employed directly as a constituent of therapeutic or cosmetic treatments, such as emulsions, lotions, sprays, ointments, creams and foam masks. Final products may contain up to 10% by weight but preferably 0.001 to 5% of such a solution though of course more concentrated or more dilute solutions may also be used in greater or lesser amounts. For example, an eye cream may comprise about 0.1% (w/w) and a facial cream may comprise about 0.01% (w/w) of a polyphenolic compound in an excipient.

A therapeutic composition of the present invention can include pharmaceutically acceptable salts of the components therein. Pharmaceutically acceptable salts include the acid addition salts that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers and excipients are well known in the art. Other equivalent terms include physiologically acceptable or tissue compatible. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Thus, the dosage ranges for the administration of polyphenolic are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted in the event of any complication.

The compositions are administered in a manner compatible with the dosage formulation, and in a therapeutically effective amount. A therapeutic amount of a polyphenolic-based composition is an amount sufficient to produce the desired result, and can vary widely depending upon the disease condition and the potency of the therapeutic compound. In the present invention the desired result is an improvement in elasticity of the tissue as determined by an improvement in the elastin content of the tissue, improved capacity and function of the tissue, or improved appearance, suppleness, and/or tone of the tissue being treated. The quantity to be administered depends on the subject to be treated, the capacity of the subject's system to utilize the active ingredient, and the degree of therapeutic effect desired. Precise amounts of active ingredient required to be administered depend on the judgment of the practitioner and are peculiar to each individual. However, suitable dosage ranges for systemic application are disclosed herein and depend on the conditions of administration. Suitable regimes for administration are also variable, but are typified by an initial administration followed by repeated doses at one or more time intervals by a subsequent administration. Where a single composition is not available for a treatment, or where such a composition is not desirable, administration of composition may also comprise the application of several different compositions sequentially to achieve a desired therapeutic effect.

Topical carriers are employed which should be both non-irritating to the skin and which are suitable for delivering the active components to the skin. Further, suitable topical carriers should be those which do not inhibit the antioxidant activity of the active ingredients thus reducing the efficiency of the composition for protecting the skin from the effects of acute and chronic ultraviolet radiation. Further, such carriers must be of sufficiently high purity and sufficiently low toxicity to render them suitable for chronic topical administration to the skin and be free of bacterial contaminants.

The active ingredients described herein can be incorporated in any suitable pharmacologically acceptable carrier which is suitable for topical administration to the human skin. As such, the pharmacologically acceptable carrier must be of sufficient purity and have sufficiently low toxicity to render it suitable for administration to a human noting that, generally, the carrier can represent up to 99.99% and typically from at least approximately 80% of the total composition. Thus, the phrase "pharmaceutically acceptable" refers to molecular entities and compositions that do not produce an allergic or similar untoward reaction when administered to a human. The pharmaceutically acceptable carriers and additives employed in the present compositions are compatible with at the tannic acid and/or ellagic acid compounds and compositions described herein containing such compounds.

Typical compositions for use herein include a wide variety of physical forms. These include, but are not limited to, solutions, lotions, creams, oils, gels, sticks, sprays, ointments, balms, patches and pastes. Generally, such carrier systems can be described as being solutions, creams, emulsions, gels, solids and aerosols.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, battalion glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated by reference.

Alternatively, the polyphenolic compound can be formulated as a lotion containing from about 0.01% to 10% of the above described active ingredients. Further, it may be formulated from a solution carrier system as a cream. A cream of the present invention would preferably comprise from about 0.1% to 15% and preferably from 1% to 5% of the above described active ingredients. Lotions and creams can be formulated as emulsions as well as solutions.

It is contemplated that the polyphenolic compounds described above may be used as a lotion or cream emulsion of the oil-in-water type or as a water-in-oil type, both of which being extremely well known in the cosmetic field. Multiphase emulsions such as the water-in-oil type is disclosed in U.S. Pat. No. 4,254,105, the disclosure of which is incorporated herein by reference, may also be employed.

It is further contemplated that the polyphenolic compounds be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

The compositions can include one or more of a variety of optional ingredients, such as, but not limited to, anti-inflammatory agents, sunscreens/sunblocks, stimulators of protein synthesis, cell membrane stabilizing agents (i.e., carnitine), moisturizing agents, coloring agents, opacifying agents and the like, so long as they do not interfere with the elastin stabilizing properties of the polyphenolic compounds, or derivatives thereof. The formulation can also include, other active ingredients, such as antibiotics, analgesics, anti-allergenics and the like. The formulation is commonly applied to the skin as a lotion or cream to be rubbed on body tissue over the desired area. For optimum efficacy treatment in accordance with the presented method should be initiated as early as possible following exposure to sunlight or other radiation source. The formulation is generally applied to the skin once or twice daily. As noted elsewhere herein, the present composition may also be used to inhibit and/or minimize the effects of aging and/or photo damage on the skin.

In the compositions provided herein the polyphenolic compounds, or derivatives thereof, such as tannic acid and/or ellagic acid, is present in an amount from about 0.01 to 80 weight percent, further from about 0.1 to 20 weight percent, and further from about 0.5 to 10 weight percent.

The optional source of small elastin-derived peptides (such as, but not limited to ProK-60 or E91) component stimulates new elastogenesis, supplementing elastic tissue, and consequently, reduction of wrinkles and other skin conditions related to loss of elasticity. The source of small elastin-derived peptides component, when used in the composition is generally present in an amount from about 0.001 to about 10 weight percent, preferably from about 0.005 to about 0.1 weight percent of the composition.

The optional manganese component may be any magnesium compound, or a pharmaceutically acceptable salt thereof, but preferably is $MnCl_1$, $MnSO_4$ and/or MnPCA, wherein the manganese component is typically present in an amount from about 0.001 to 10 weight percent, preferably from about 0.0012 to 0.012 weight percent of the composition.

A trivalent iron component, such as, but not limited to, Ferric Ammonium Citrate (FAC) may also be included in the composition. The trivalent iron component stimulates new elastogenesis and assists in treatment of elastic tissue defects. The trivalent iron, when included in the composition, is generally present in an amount from about 0.001 to about 10 weight percent of the composition.

Copper may also be included in the composition. In preferred embodiments, copper may be present in about 0.001 to about 10 weight percent, more preferably from about 0.005 to about 0.1 weight percent of the composition.

Elastogenic plant-derived peptides may also be present in the composition. Such peptides are more fully described in U.S. Provisional Patent Application No. 60/671,557 filed Apr. 15, 2005 entitled "Plant-Derived Elastin Binding Protein Ligands and Methods of Using the Same", U.S. Provisional Application No. 60/681,600 filed May 17, 2005 entitled "Proteolytic Digest Derived from Bovine Ligamentum Nuchae Stimulates Deposition of New Elastin-Enriched Matrix in Cultures and Transplants of Human Dermal Fibroblasts" and U.S. Provisional Patent Application No. 60/737,586 filed Nov. 17, 2005 entitled "Plant-Derived Elastin Binding Protein Ligands and Methods of Using the Same. Such peptides may be sextapeptide comprising the sequence $X_1$-$X_2$-$X_3$-$X_4$-$X_5$-$X_6$, wherein $X_1$ is V or 1, $X_2$ is G, $X_3$ is A, L or V, $X_4$ is M, S, or A, $X_5$ is P and $X_6$ is G. Such a plant-derived peptide or synthetic plant-derived peptide may be present in the composition. In preferred embodiments, the peptide may be present in about 0.0001 to about 0.01 weight percent, more preferably from about 0.0004 to about 0.002 weight percent of the composition.

Upon formulation, compositions of the present invention may be administered in a manner compatible with the dosage formulation and in such amount as is therapeutically effective. The formulations are easily administered in a variety of dosage forms such as direct topical application, application via a transdermal patch and the like.

For topical administration in an aqueous solution, for example, the compositions may be used directly on the skin without any toxic effects to the patient. Alternatively, the compositions of the invention may be dissolved or resuspended in a suitable buffer prior to mixing, if necessary.

In general, routine experimentation will determine specific ranges for optimal therapeutic effect for each composition and each administrative protocol, and administration to specific individuals will be adjusted to within effective and safe ranges depending on the condition and responsiveness of the individual to initial administrations.

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description.

Example 1

Materials. All chemical-grade reagents were obtained from Sigma (St. Louis, Mo.). αMEM medium, fetal bovine serum (FBS), 0.2% trypsine-0.02% EDTA and other cell culture products were obtained from GIBCO Life Technologies (Burlington, Canada). Polyclonal antibody to tropoelastin and BA4 monoclonal antibody to VGVAPG (SEQ ID NO: 1) were purchased from Elastin Products Company, Inc. (Owensville, Mo.). Monospecific polyclonal anti-AKAAA-KAAAKA antibody was a gift of Dr. Barry Starcher from the University of Texas. Secondary antibody fluorescein-conjugated goat anti-rabbit (GAR-FITC) was purchased from Sigma (St. Louis, Mo.). DNeasy Tissue system for DNA assay and RNeasy Mini Kit for isolation of total RNA were purchased from Qiagen (Mississauga, Canada). Expression probe for elastin was purchased from Applied Biosystems (Foster City, Calif.). The radiolabeled reagents, [$^3$H]-valine, and [$^3$H]-thymidine were purchased from Amersham Canada Ltd. (Oakville, Canada).

Cell Cultures. Biological effects of ellagic acid and tannic acid were tested in cultures of dermal fibroblasts derived from punch biopsies of healthy skin from Caucasian females of different ages ranging from 4-52 years old. All fibroblasts were originally isolated by allowing them to migrate out of skin explants and then passaged by trypsinization and maintained in alpha-minimum essential medium supplemented with 20 mM Hepes, 1% antibiotics and antimycotics, 1% L-Glutamate and 2% fetal bovine serum (FBS). In all experiments, consecutive passages 3-5 were tested. Cells were densely plated ($50 \times 10^5$ cells/dish) to reach confluency and then cultured for 7 days in the presence and absence of ellagic acid (dissolved in DMSO) and tannic acid (dissolved in water), both in concentration of 1 µg/mL. This optimal concentration was chosen after a series of pilot experiments indicated that 1 µg/ml of EA and TA induced optimal effect on net deposition of elastin and did not trigger any change in cellular proliferation rate nor affect basic metabolic performance.

In a parallel series of experiments, cultures of dermal fibroblasts were treated with well established stimulators of tropoelastin synthesis, ProK-60 (25 µg/ml) and Ferric Ammonium Citrate (20 µM), and simultaneously incubated in the presence and absence of ellagic acid or tannic acid (both in concentration 1 µg/ml).

Assessment of Cellular Proliferation. Cellular proliferation rates of control, ellagic acid and tannic acid treated fibroblasts were assessed at the end point by counting of trypsinized cells, by total DNA assay using the DNeasy Tissue System from Qiagen and by assessment of [$^3$H]-thymidine incorporation, which was added to all cultures (2 µCi/well) for the last 24 hours.

Assessment of Elastin mRNA levels. Fibroblasts were cultured to confluency in medium with 2% FBS and then in serum-free medium for 24 hours. The medium was changed again and cells were incubated for the next 24 hours in the presence and absence of ellagic acid or tannic acid (both in concentration 1 µg/mL). At the end of the incubation period total RNA was extracted using TRI-reagent. Steady-state levels of elastin mRNA were analyzed by semi quantitative PCR and by Northern Blot using a human elastin cDNA recombinant H-11 probe. In all experiments, performed in triplicate, the loading control was routinely performed.

Assessment of elastic fibers content by immunohistochemistry. Seven-day-old and 14-day-old confluent cultures of fibroblasts, which produce abundant ECM, were assessed. All cultures were fixed in cold 100% methanol at −20° C. for 30 min, then incubated for 1 hour with 2 µg/ml of polyclonal antibody to tropoelastin. Cultures were then incubated for an additional hour with appropriate fluorescein-conjugated secondary antibody (GAR-FITC). Nuclei were counterstained with propidium iodide. Morphometric analysis of five separate cultures in each experimental group, immunostained with antibodies recognizing extracellular matrix components was performed using a computerized video analysis system (Image-Pro Plus software 3.0, Media Cybernetics, Silver Spring, Md.).

Radioactive metabolic labeling and quantification of newly deposited insoluble elastin. Quintuplicate, 4 day-old cultures of dermal fibroblasts maintained in the presence or absence of 1 µg/mL of ellagic acid or tannic acid were additionally exposed for the 3 following days to 20 µCi [$^3$H]-valine. At the end of incubation period the contents of radioactive NaOH-insoluble elastin was assessed separately in each culture by scintillation county. Final results reflecting amounts of metabolically labeled, insoluble elastin were expressed as CPM/µg DNA. DNA was determined with the DNeasy Tissue System from Qiagen Proteolytic Pulse and chase experiments aimed at the assessment of durability of newly deposited metabolically-labeled elastin. In this series of experiments, dermal fibroblasts, plated as described above in media with 10% FBS, were maintained in the presence and absence of 1 µg/mL of EA or TA for the first 7 days and pulsed with 20 µCi [$^3$H]-valine between day 4 and 7. While quadruplicate 7-day-old cultures from each experimental group were directly processed for the assessment of radioactive NaOH-insoluble elastin, parallel quadruplicate cultures from each experimental group were transferred to media containing only 1% FBS, which did not stimulate proliferation and new elastogenesis, and maintained for the next seven days (chase period) in the absence of ellagic acid or tannic acid. At day 14 these cultures were terminated and the net content of the radioactive NaOH-insoluble elastin was assessed as described above.

Organ cultures of explants derived from surgical biopsies of human skin In order to further test whether ellagic acid and tannic acid would penetrate into skin tissue and enhance elastogenesis, fragments of normal skin (from 30 and 34 year old females) obtained during plastic surgery procedures were tested in organ culture system. Skin fragments were cut into multiple 1 mm$^2$ pieces and placed on top of metal grids immersed in culture medium containing 5% FBS and maintained for 10 days in the presence and absence of 1 µg/mL of ellagic acid or tannic acid alone or combined with 25 µg/ml of ProK-60. The media were changed every second day. All organ cultures were fixed in 1% buffered formalin and their transversal serial histological sections were stained with Movat's pentachrome. Morphometric analysis was performed as described above. In each analyzed group (three explants from each patient) low-power fields (1 mm$^2$) of 20 serial sections stained with Movat's pentachrome were analyzed and all structures stained black (elastic fibers) were counted.

Assessment of tropoelastin integrity by western blots. To determine the influence of tannic acid and ellagic acid on the integrity of soluble tropoelastin, dermal fibroblasts obtained from three different donors (initially plated at 50,000 cells/dish) were cultured to confluency in medium with 5% FBS and then triplicate cultures were incubated for the next 24 hours in the presence and absence of ellagic acid or tannic acid (both in concentration 1 µg/mL). At the end of the incubation period conditioned media were collected and then the soluble proteins present in the intracellular compartments were extracted with 0.5 M acetic acid in the presence of proteinase inhibitors in the following final concentrations: 2 mM benzamidine, 2 mM EACA, 2 mM PMSF, 1 mM EDTA and 1 mg/ml Trasylol. Extraction was carried out for six hours at 4° C. and the insoluble material was pelleted by centrifugation. The supernatant was dialyzed exhaustively (4000 kDa cutoff membrane) at 4° C. against water containing proteinase inhibitors, then lyophilized. Concentrated preparations of the conditioned media and cell extracts from all analyzed cultures were analyzed for their protein content, and then samples containing equal amounts of protein (20 µg/sample) were suspended in 2×SDS sample buffer with DTT, resolved by SDS PAGE, routinely transferred to nitrocellulose and immunoblotted with specific anti-tropoelastin antibody.

Immuno-precipitation of radioactive tropoelastin-like peptides. This experiment was aimed at elucidating whether binding of ellagic acid or tannic acid to tropoelastin molecules would block two characteristic elastin domains responsible for orderly self-aggregation and cross-linking respectively. Instead of very unstable tropoelastin, triplicate samples of a [$^3$H]-valine-labeled recombinant polypeptide containing linear amino acid sequences encoded by human tropoelastin gene exons; 20-(21-23-24)$_2$ were used. 100 µl samples of this radioactive recombinant polypeptide modeled after human elastin dissolved in PBS (specific radioactivity 1000 CPM/sample) were incubated in the presence and absence of 1 µg/mL of ellagic acid or tannic acid, at room temperature for 6 hours. Aliquots of all control and experimental samples were then immuno-precipitated with (BA4) monoclonal antibody (recognizing VGVAPG (SEQ ID NO: 1) and other similar domains, encoded by exons 20 (SEQ ID NO: 2) and 24 (SEQ ID NO: 3), responsible for self-aggregation of tropoelastin) and with monospecific polyclonal anti-AKAAAKAAAKA antibody recognizing the exon 21- (SEQ ID NO: 4) and 23-(SEQ ID NO: 5) encoded cross-linking sequences. It was anticipated that in case that binding of ellagic acid or tannic acid would block one or both of these crucial domains present in the tested radioactive recombinant peptide, it could not be immunoprecipitated with anti-VGVAPG or anti-AKAAAKAAAKA antibodies.

Proteolytic degradation protection assay of insoluble elastin. To determine whether ellagic acid or tannic acid may directly protect fully cross-linked "insoluble elastin" against elastolytic activity of several elastases, an in vitro assay measuring degradation of an insoluble [$^3$H]-elastin substrate was used. Briefly, insoluble elastin was purified from bovine ligamentum nuchae using a modification of the hot alkali technique and was shown by amino acid analysis to be free of microfibrillar protein and other contaminants. Sequencing of insoluble, digested elastin was performed using an Applied Biosystems model 473A protein sequencer equipped with a model 610A data analysis program. The stock of this pure insoluble elastin preparation was washed twice with water and twice with acetonitrile and then labeled with sodium [$^3$H]-borohydride and stored at −20° C. Before each experiment, the [$^3$H]-elastin substrate suspended in PBS was boiled for 5 min and extensively washed to remove all unbound radioactivity. Then, its 100 µg aliquots (specific activity 300 CPM/1 µg) were suspended in serum free culture medium and pre-incubated for 1 hour in the presence and absence of 1 µg/mL or 10 µg/mL of ellagic acid or tannic acid. All samples of radioactive elastin were then submitted to three 5 min washes in serum free culture medium prior to their 18 hour incubation at 37° C. with aliquots (50 ng) of human leukocyte elastase (HLE), porcine pancreatic elastase (PPE), MMP-2, or Papaine dissolved in the assay buffer (50 mM Tris-HCL, pH 7.5 containing 150 mM NaCl, 10 mM CaCl$_2$, 0.02% Brij and 0.02% sodium azide). Each treatment was tested in quadruplicate samples. At the end of the incubation, all samples were microcentrifuged (8000×g for 5 min) and 100 µl aliquots of supernatant containing the solubilized degradation products were mixed with 4 ml scintillation fluid and counted in triplicates in liquid scintillation counter. The radioactivity (cpm/sample) released into the supernatant reflecting the degradation of [$^3$H]-elastin substrate was assessed and the mean and standard deviations were calculated from sixtiplicate assessments from 3 different experiments Assessment of TA and EA binding to insoluble elastin. In order to directly show that both polyphenols bind to elastin, triplicate (1 mg) aliquots of our above mentioned preparation of pure insoluble elastin were incubated with 20 µg/ml of ellagic acid or tannic acid for 2 hr at 37° C. The initial concentration of both polyphenols were confirmed by a direct spectrophotometric reading at 280 nm. This method demonstrated a dose-dependent linear increase in absorbancy. At the end of incubation period the insoluble elastin slurries were separated by centrifugation and the concentrations of polyphenols in supernatants were determined again. The detected differences between the initial and final concentration of polyphenols in supernatants from particular samples directly indicated that both ellagic acid and tannic acid bound to elastin slurries during the incubation period. In each experimental group means±SD were calculated and obtained values were statistically compared with beginning concentrations of both polyphenols.

Statistical analysis. In all above mentioned quantitative assays, means and standard deviations (expressed as Mean±SD) were calculated and statistical analyses were carried out by ANOVA to establish whether detected differences were statistically significant.

Results.

Ellagic acid and tannic acid enhance deposition of elastin by dermal fibroblasts. Results of immunohistochemical analysis (FIGS. 1a and b) and quantitative assessment of metabolically labeled insoluble elastin (FIG. 1c) indicated that 7 day old monolayer cultures of dermal fibroblasts maintained with ellagic acid or tannic acid contain thicker elastic fibers and a higher net content of NaOH-insoluble elastin than untreated control cultures. Moreover, results of morphometric analysis demonstrated that both ellagic acid and tannic acid caused a significant (p<0.005) increase (67±6% and 96±12% respectively) in net elastogenesis observed in organ cultures of human skin explants maintained for 10 days with 5% FBS. Explants maintained for 10 days in culture media containing tannic acid contain thicker and longer elastic fibers than those present in explants maintained only in control medium or medium with ProK-60 (data not shown). Interestingly, the presence of tannic acid seems to particularly enhance elastogenesis in cells protruding from the stratum basale, toward the papillary dermis, and in cells surrounding small capillaries. Results of semi-quantitative PCR and Northern blotting indicated, however, that treatment of cultured dermal fibroblasts with ellagic acid or tannic acid did not induce any increase in the transcription of their elastin gene (data not shown) nor change their proliferation rate, as assessed by incorporation of radioactive thymidine and total DNA content (data not shown). Despite this finding, results of western blotting, with anti-tropoelastin antibody, showed that both cell extracts and conditioned media, of dermal fibroblasts incubated with ellagic acid or tannic acid, contained more intact 70 kDa tropoelastin and less immuno-detectable degradation products of lower molecular weight than untreated counterparts (data not shown). This finding gave evidence that both polyphenols protected newly produced tropoelastin from premature intracellular and pericellular degradation by endogenous proteinases.

Figure 2:
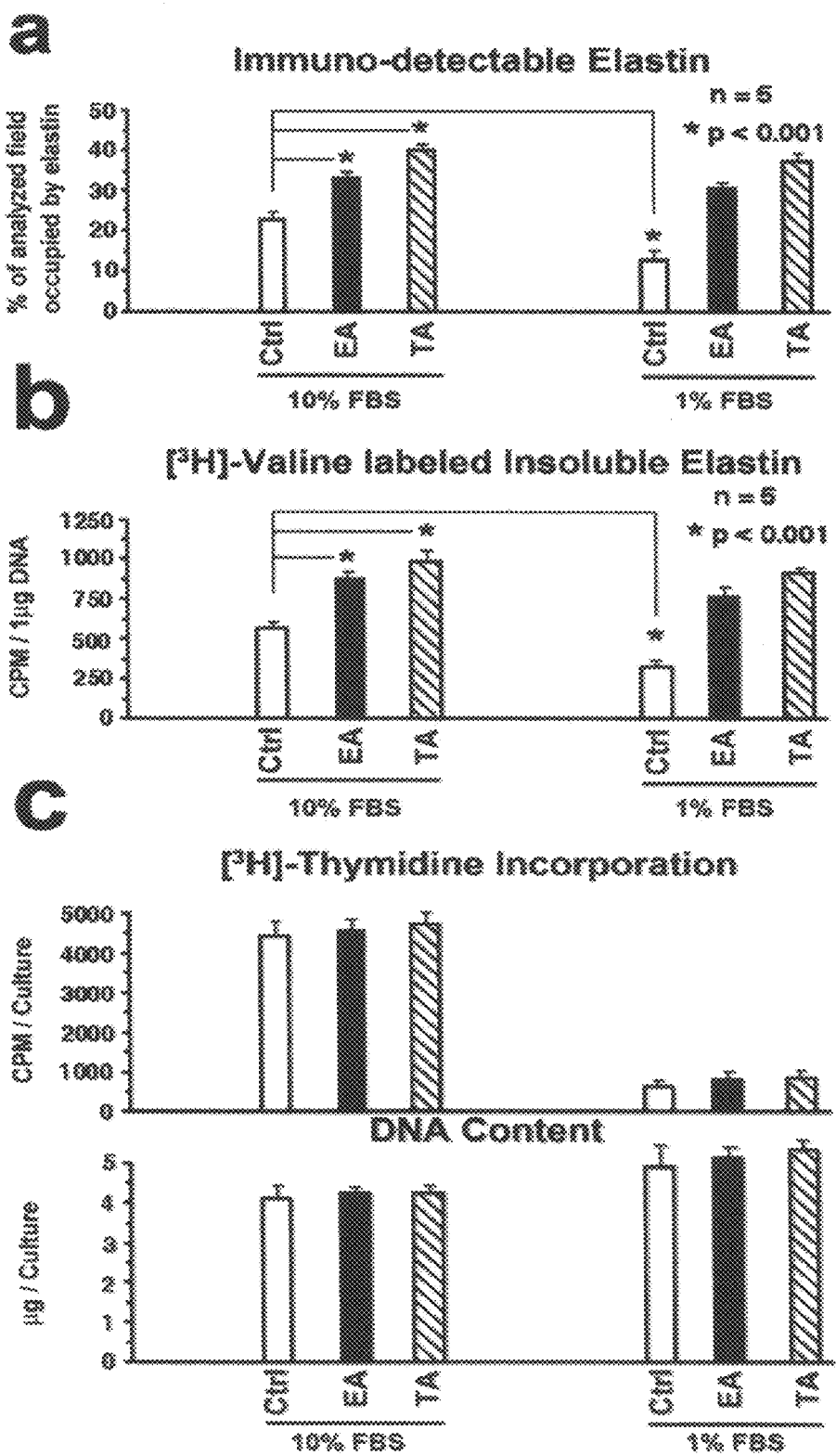
FIG. 2. Pulse and chase experiment to evaluate pretreated tropoelastin/elastin stability against non-specific enzymatic degradation. (a) Results of morphometric assessment of immuno-detectable elastin and (b) content of metabolically labeled insoluble elastin, detected at the respective ends of the indicated pulse and chase periods, demonstrate that cultures of dermal fibroblasts derived from a 26 year-old female, that were incubated the first seven days in the presence of EA and TA (1 μg/mL each), sustain their high net content of insoluble elastin (metabolically pulsed with [$^3$H]-valine between day 4 and 7) even when maintained for an additional seven days (chase period) in media containing only 1% FBS and no polyphenols. In contrast, 14 day-old control (untreated) cultures demonstrate a significant decrease in their net content of metabolically labeled insoluble elastin (initially deposited at the end of pulse period, at day 7). (c) The assessment of [$^3$H]-thymidine incorporation and assay of total DNA indicate that conditions of the chase period in which cells were maintained in 1% FBS caused inhibition of cellular proliferation.
Figure 3:
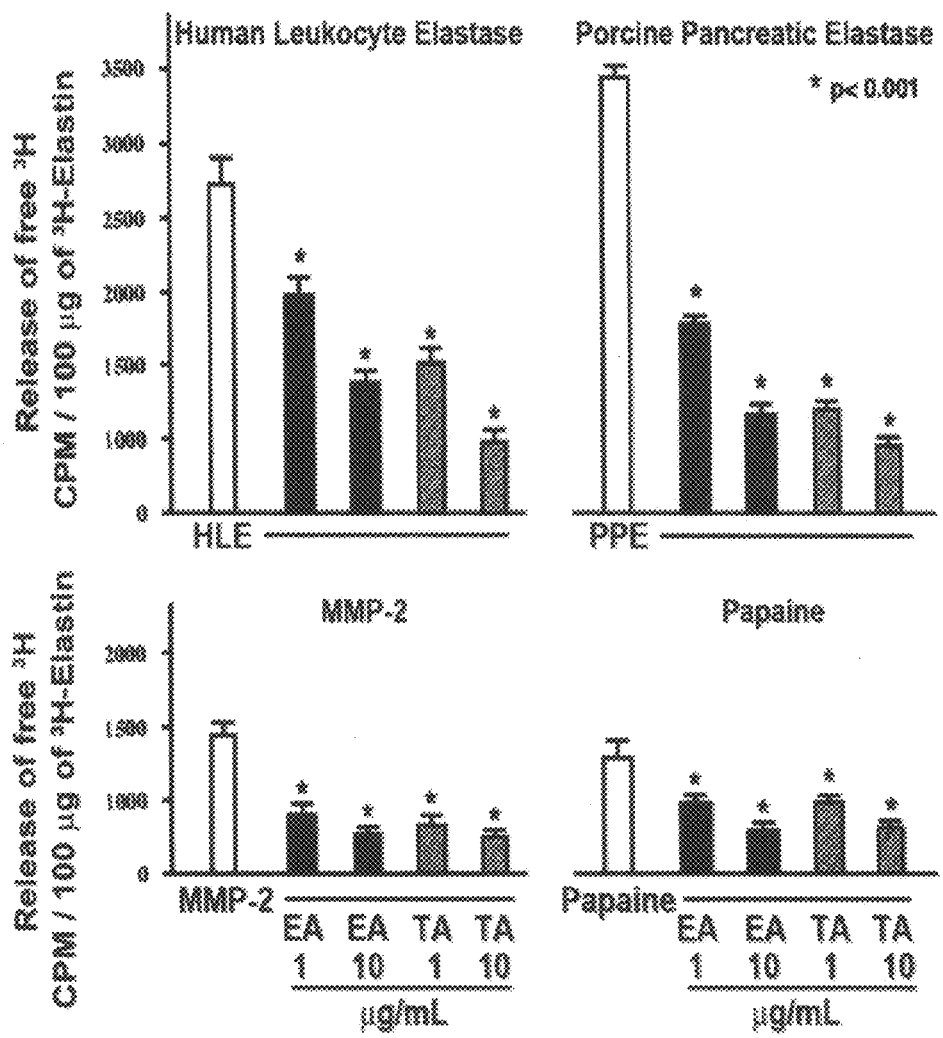
FIG. 3. Evaluation of the protective effect of polyphenols against elastolytic degradation of insoluble elastin. Results of in vitro assay demonstrate that samples of insoluble [$^3$H]-labeled elastin from bovine ligamentum nuchae, pretreated with EA or TA (1 μg/mL and 10 μg/mL each) demonstrate higher resistance to proteolytic degradation by indicated enzymes belonging to three different classes of proteinases (elastases) capable of elastin degradation.

Ellagic acid and tannic acid protect elastin from proteolytic degradation. Results of a pulse and chase experiment (FIGS. 2a and b) demonstrated that cultures of dermal fibroblasts, exposed for seven days to ellagic acid and tannic acid, sustain their high net content of insoluble elastin (metabolically pulsed with [$^3$H]-valine between day 4 and 7) when maintained for an additional seven days (chase period) in media containing only 1% FBS (no ellagic acid or tannic acid), which did not stimulate proliferation (FIG. 2c) and new elastogenesis. In contrast, 14 day-old control (untreated) cultures demonstrated a significant decrease in their net content of metabolically labeled insoluble elastin (detected at the end of pulse period, at day 7). Moreover, results of an in vitro elastolytic assay demonstrated that samples of purified insoluble elastin (purity confirmed by amino acid analysis), pretreated with ellagic acid or tannic acid, were more resistant to proteolytic degradation by all tested elastolytic enzymes belonging to the serine proteinase (human leukocyte elastase and porcine pancreatic elastase), metallo-proteinase (MMP-2) and cysteine proteinase (papaine) families (FIG. 3). These data suggested that ellagic acid and tannic acid protected newly deposited and purified insoluble elastin against degradation by both endogenous and exogenous elastolytic enzymes, respectively, through association with elastin.

Ellagic acid and tannic acid bind to elastin and tropoelastin. Results of a spectrophotometric assay (displaying a linear concentration curve for both ellagic acid and tannic acid at an absorbance of 280 nm), comparing concentrations of both polyphenols before and after incubation with insoluble elastin, demonstrated that 1 mg of pure insoluble elastin, isolated from ligamentum nuchae, absorbed 87±3% of the tannic acid and 81±2% of the ellagic acid in solutions having had initial concentrations of 20 µg/mL of each polyphenol. This finding implied that both polyphenols bind to insoluble elastin. Additional results showed that preincubation of a [$^3$H]-valine-labeled recombinant peptide, containing the most characteristic hydrophobic and cross-link generating domains of tropoelastin, with ellagic acid and tannic acid did not preclude its effective (practically identical) immunoprecipitation with respective anti-VGVAPG and anti-AKAAAKAAAKA antibodies (data not shown). This indicated that these polyphenols associate with and protect tropoelastin in a way which does not obscure hydrophobic domains (eg. VGVAPG (SEQ ID NO: 1), necessary for self-aggregation, nor KAAAK (SEQ ID NO: 6) sequences participating in crosslinking.

Figure 4:
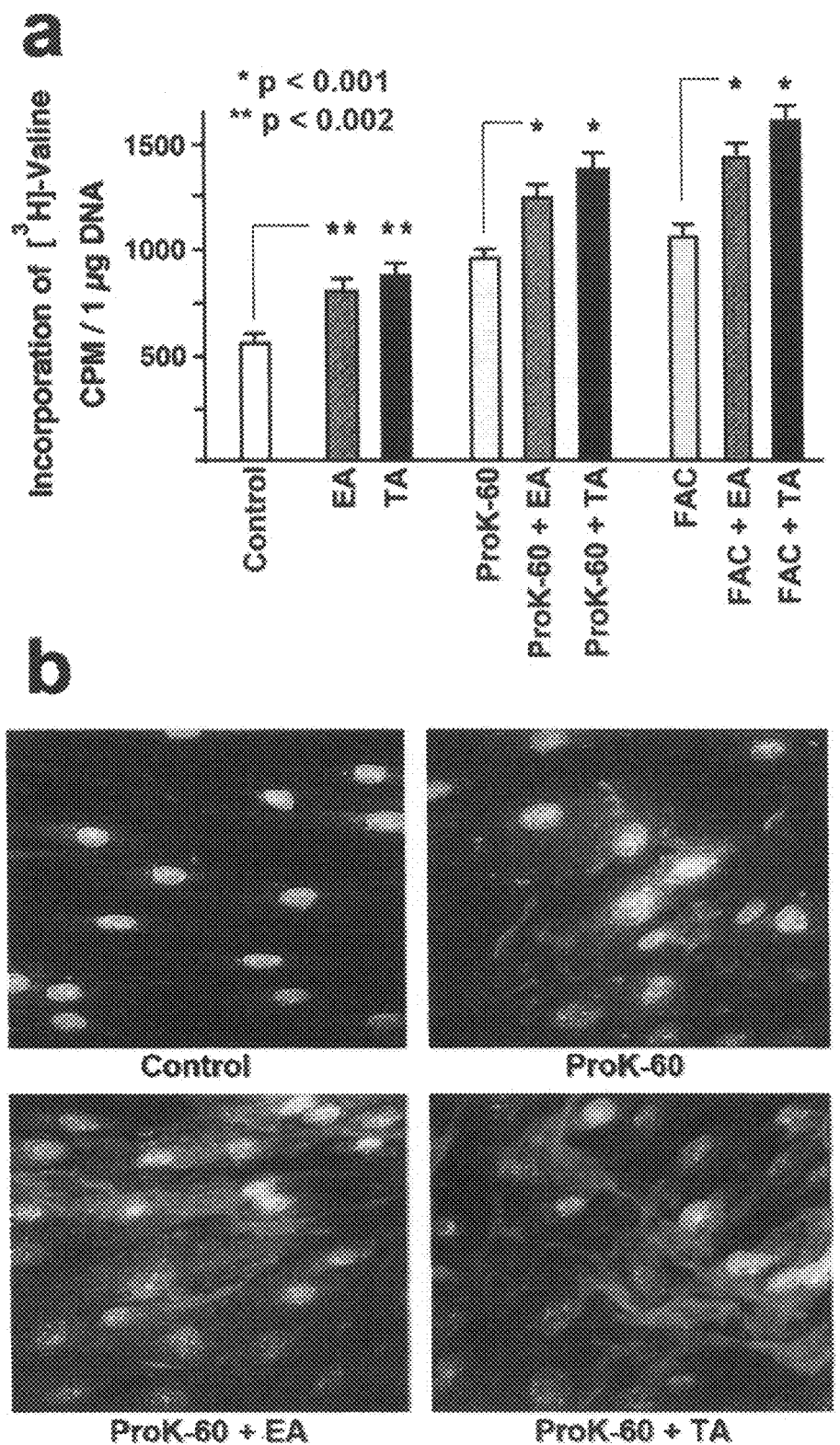
FIG. 4. Assessment of the effect of polyphenols on elastogenesis induced by known elastogenic compounds. (a) Results of the quantitative assessment of newly deposited insoluble elastin (metabolically labeled with [$^3$H]-valine) detected in 7 day-old cultures of dermal fibroblasts derived from a healthy 50 year-old caucasian female. Fibroblasts maintained in the presence of stimulators of elastin synthesis, mixture of small elastin-derived peptides (ProK-60 25 μg/mL) or Ferric Ammonium Citrate (FAC 20 μM), significantly increased their net deposition of insoluble elastin as compared with the untreated control. Additional treatment either with ellagic acid (1 μg/mL) or tannic acid (1 μg/mL) cause further proportional increase in net elastin content in all tested experimental groups. (b) Representative micrographs of 7 day-old cultures of dermal fibroblasts (derived from 50 year-old caucasian female) immuno-stained with anti tropoelastin antibody. Cultures treated with ProK-60 (25 μg/mL) produced more elastic fibers than untreated control cultures. Additional treatment either with ellagic ecid (EA) or with tannic acid (TA) (both in concentration 1 μg/mL) caused a further increase in net deposition of immunodetectable elastic fibers.

Ellagic acid and tannic acid enhance elastogenic effect of selected stimulators of elastogenesis. Results of immunostaining and metabolic labeling established that addition of ellagic acid or tannic acid to fibroblast cultures simultaneously treated with known stimulators of elastin gene expression, ProK-60 or Ferric Ammonium Chloride (FAC), significantly enhanced their net deposition of insoluble elastin as estimated in 7 day old monolayer cultures (FIG. 4). Morphometric analysis additionally demonstrated that both polyphenols significantly ($p<0.02$) enhanced elastogenic effect of ProK-60 observed in 10 day-old organ cultures of human skin explants (Ellagic Acid=22±4% and Tannic Acid=35±6%). Representative micrographs depicting synergistic effect of ProK-60 and tannic acid are presented in FIG. 4d.

Discussion. Results demonstrate that the two polyphenols, ellagic acid and tannic acid, used in concentration of 1 µg/ml, did not modulate cellular proliferation of normal human dermal fibroblasts, despite the fact that anti-proliferative properties of both of these compounds were reported in cultures of various normal and malignant cell lines when used in higher doses. Dermal fibroblasts treated with both acids did not demonstrate any increase in levels of elastin mRNA yet facilitated a significant increase in net elastic fiber content detected by immunochemistry and metabolic labeling of insoluble elastin. It was speculated that both ellagic acid and tannic acid might bind to intracellular tropoelastin and to newly assembled crosslinked elastin and protect them from proteolytic degradation by fibroblast-secreted proteolytic enzymes engaged in early remodeling of extacellular matrix. The hypothesis regarding potential preferential binding of both polyphenols to intracellular tropoelastin and extracellular elastin polymer was based on a previously described observation that addition of 0.25% tannic acid to glutaraldehyde fixative dramatically enhanced contrast of intracellular secretory vesicles containing tropoelastin and contrast of extracellular elastic fibers in tissues observed under the electron microscope. In fact, in the pre-immunostaining era, treatment with tannic acid became a widely accepted method for ultrastructural identification of elastic fibers that were previously described as "electron lucent and amorphous" under electron microscopy. The hypothesis was further supported by results of our pulse-and-chase experiment where ellagic acid and tannic acid pre-treated tropoelastin and insoluble elastin, deposited by dermal fibroblasts, remained resistant against non-specific endogenous degradation in the absence of ellagic acid or tannic acid in culture medium. Results also show that pre-incubation of [$^3$H]-labeled pure insoluble elastin, with either ellagic acid or tannic acid, significantly reduced its rate of degradation (in the absence of either polyphenol in the digest buffer) by several exogenous elastolytic enzymes including porcine pancreatic elastase, human leukocyte elastase, papaine and the UVB-inducible MMP-2. Results of this protection assay are consistent with recent observations that addition of tannic acid to the glutaraldehyde fixation process increased the stability of porcine aortic explants exposed to pancreatic elastase digestion. Moreover, the spectrophotometric study demonstrated that pure insoluble elastin, isolated from ligamentum nuchae, binds both ellagic acid and tannic acid, sequestering them from their solvent solutions. Results of this study are in further agreement the observation of similar binding of tannic acid by pure aortic elastin over time.

It has been previously shown that plant derived polyphenols, tannins and their synthetic derivatives, can inhibit human leukocyte elastase and MMP-2/-9 activity in several tumor cells. Other studies directly demonstrated that tannic acid specifically inhibits the chymotrypsin-like activity of purified 20S proteasomes and the activity of tissue-type plasminogen activator, urokinase-type plasminogen activator and plasmin activity. It was speculated that a certain fraction of the described protective effect may be due to a direct inhibition of proteolytic enzymes by both polyphenols absorbed by or released from the elastin substrate.

The practical biological significance of the observations is that ellagic acid or tannic acid added to cultures of living cells facilitate normal secretion of tropoelastin and its assembly into elastic fibers by protecting intra- and extracellular tropoelastin from degradation by unspecific proteinases. Since ellagic acid and tannic acid did not block domains responsible for self-aggregation and subsequent cross-linking of this protein, it is speculated that ellagic acid and tannic acid may act in concert with the 67-kDa elastin binding protein (EBP) that acts as a protective molecular chaperone for intracellular tropoelastin. Moreover, the fact that ellagic acid and tannic acid significantly decreased degradation of newly produced elastin, in dermal fibroblast cultures, and fully cross-linked elastin, from ligamentum nuchae, indicate that both polyphenols may enhance longevity of elastic fibers.

Given the presented beneficial effects of both tested polyphenols, both may be used in topical preparations aimed at prevention of elastin degradation characteristic of normal aging and after chronic exposure to sunlight (photoaging). Since ellagic acid and tannic acid did not negatively interfere with the action of two known stimulators of new elastogenesis, but rather enhanced their net effect, their use in combination with compounds aimed at restoring cutaneous elastic fibers in aged skin or skin of patients afflicted by diseases caused by elastin gene insufficiency (i.e. Williams-Beuren Syndrome (WBS) and Cutis Laxa) may also appear beneficial. Results of our recent experiments (data not shown) indicated that tannic acid and ellagic acid prevented rapid, MMP-dependent degradation of tropoelastin produced by dermal fibroblasts derived from three WBS patients, yielding a significant (21-26%) net increase in deposition of insoluble elastin by these cells. Thus, results of the in vitro studies, presented herein, and lack of clinical side effects of polyphenolic compounds fully encourage their use in in vivo protection of existing elastic fibers and more efficient elastogenesis in skin.

In summary, results of in vitro studies demonstrate the use of tannic acid and ellagic acid and other polyphenolic compounds in skin care products aimed at initiation of new elastogenesis and protection of existing elastic fibers from normal aging-related and UV-induced proteolytic degradation.

Example 2

In order to directly prove that tannic acid also binds to collagen type I, triplicate (1 mg) aliquots of pure collagen type I were incubated with 20 µg/ml of TA for 2 h at 37° C. The initial concentration of tannic acid was confirmed by direct spectrophotometric reading at 280 nm. This method adopted from Gori et al. demonstrated a dose-dependent linear increase in absorbance. At the end of incubation period the collagen type I slurries were separated by centrifugation and the concentration of tannic acid in supernatants were spectrophotometrically determined again at 280 nm. In each experimental group means±SD were calculated and obtained values were statistically compared with beginning concentrations of both polyphenols.

Figure 5:
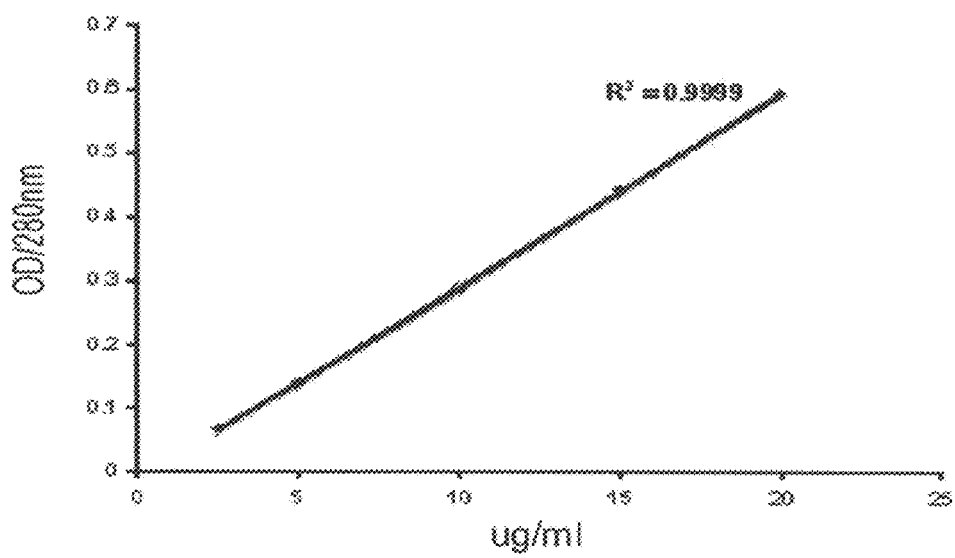
FIG. 5. Assessment of binding of tannic acid to collagen type I. (a) Results of triplicate (1 mg) aliquots of pure collage type I incubated with 20 μg/ml of tannic acid for 2 hour at 37° C. Initial concentration of tannic acid was confirmed by direct spectrophotometric reading at 280 nm. This method demonstrated a dose-dependent linear increase in absorbance. At the end of incubation period the collagen type I slurries were separated by centrifugation and the concentration of TA in supernatants were spectrophotometrically determined again at 280 nm. In each experimental group means±SD were calculated and obtained values were statistically compared with beginning concentrations of both polyphenols. (b) 1 mg of collagen type I (from rat tail) sequestered 75.5±0.001% (P<0.0001) of the TA (originally 20 μg/mL) from solution, suggesting that tannic acid may also bind to collagen type I.
Figure 5:
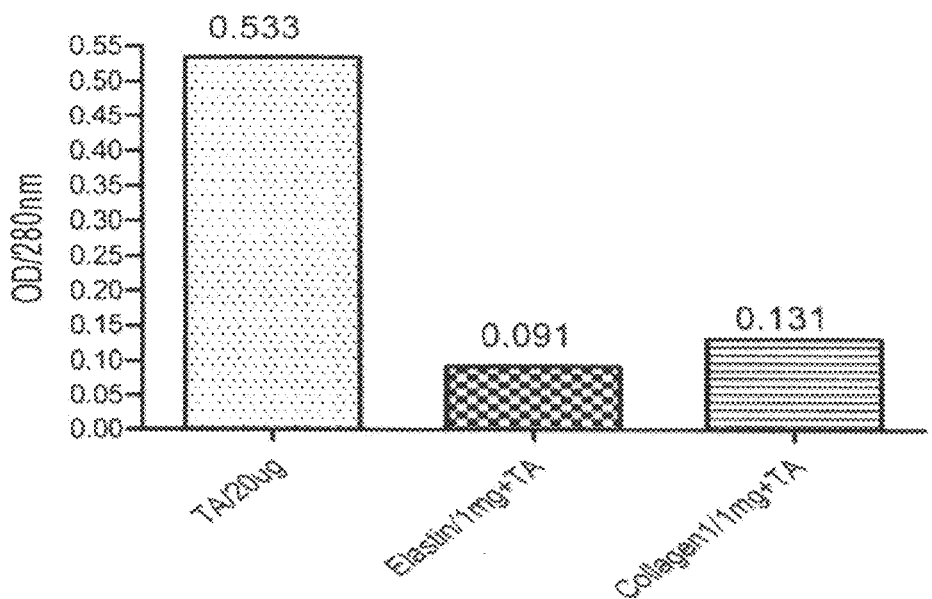

Results. As shown in FIG. 5, the binding studies demonstrate that 1 mg of collagen type I (from rat tail) sequestered 75.5±0.001% (P<0.0001) of the tannic acid (originally 20 µg/mL) from solution, suggesting that tannic acid may also bind to collagen type I.

What is claimed is:

1. A method for reducing photo-induced damage to the skin comprising administering an effective amount of a polyphenolic compound and a peptide selected from the group consisting of SEQ ID NO: 1 (Val-Gly-Ala-Met-Pro-Gly), SEQ ID NO: 2 (Val-Gly-Leu-Met-Pro-Gly), SEQ ID NO: 3 (Val-Gly-Val-Met-Pro-Gly), SEQ ID NO: 4 (Val-Gly-Ala-Ser-Pro-Gly), SEQ ID NO: 5 (Val-Gly-Ala-Ala-Pro-Gly), SEQ ID NO: 6 (Val-Gly-Leu-Ser-Pro-Gly), SEQ ID NO: 7 (Val-Gly-Leu-Ala-Pro-Gly), SEQ ID NO: 8 (Val-Gly-Val-Ser-Pro-Gly), SEQ ID NO: 9 (Ile-Gly-Ala-Met-Pro-Gly), SEQ ID NO: 10 (Ile-Gly-Leu-Met-Pro-Gly), SEQ ID NO: 11 (Ile-Gly-Val-Met-Pro-Gly), SEQ ID NO: 12 (Ile-Gly-Ala-Ser-Pro-Gly), SEQ ID NO: 13 (Ile-Gly-Ala-Ala-Pro-Gly), SEQ ID NO: 14 (Ile-Gly-Leu-Ser-Pro-Gly), SEQ ID NO: 15 (Ile-Gly-Leu-Ala-Pro-Gly), SEQ ID NO: 16 (Ile-Gly-Val-Ser-Pro-Gly), SEQ ID NO: 17 (Ile-Gly-Val-Ala-Pro-Gly) and combinations thereof wherein the photo-induced damage to the skin is reduced.

2. The method of claim 1, wherein said polyphenolic compound is selected from tannic acid, ellagic acid and combinations thereof.

3. The method of claim 1, wherein said effective amount of said polyphenolic compound is from about 1 µg to about 10 µg.

4. The method of claim 1 further comprising administering a stimulator of elastogenesis selected from elastin-derived peptides, plant-derived peptides, bovine-derived peptides, manganese, iron, copper and combinations thereof.

5. The method of claim 4, wherein said polyphenolic compound and said stimulator of elastogenesis are administered simultaneously.

6. The method of claim 4, wherein said polyphenolic compound and said stimulator of elastogenesis are administered sequentially.

7. The method of claim 1, wherein said polyphenolic compound and said peptide are administered simultaneously.

8. The method of claim 1, wherein said polyphenolic compound and said peptide are administered sequentially.

9. A method for protecting dermal tissue from damage by irradiation comprising administering an effective amount of a polyphenolic compound and a peptide selected from the group consisting of SEQ ID NO: 1 (Val-Gly-Ala-Met-Pro-Gly), SEQ ID NO: 2 (Val-Gly-Leu-Met-Pro-Gly), SEQ ID NO: 3 (Val-Gly-Val-Met-Pro-Gly), SEQ ID NO: 4 (Val-Gly-Ala-Ser-Pro-Gly), SEQ ID NO: 5 (Val-Gly-Ala-Ala-Pro-Gly), SEQ ID NO: 6 (Val-Gly-Leu-Ser-Pro-Gly), SEQ ID NO: 7 (Val-Gly-Leu-Ala-Pro-Gly), SEQ ID NO: 8 (Val-Gly-Val-Ser-Pro-Gly), SEQ ID NO: 9 (Ile-Gly-Ala-Met-Pro-Gly), SEQ ID NO: 10 (Ile-Gly-Leu-Met-Pro-Gly), SEQ ID NO: 11 (Ile-Gly-Val-Met-Pro-Gly), SEQ ID NO: 12 (Ile-Gly-Ala-Ser-Pro-Gly), SEQ ID NO: 13 (Ile-Gly-Ala-Ala-Pro-Gly), SEQ ID NO: 14 (Ile-Gly-Leu-Ser-Pro-Gly), SEQ ID NO: 15 (Ile-Gly-Leu-Ala-Pro-Gly), SEQ ID NO: 16 (Ile-Gly-Val-Ser-Pro-Gly), SEQ ID NO: 17 (Ile-Gly-Val-Ala-Pro-Gly) and combinations thereof wherein the dermal tissue is protected from damage by irradiation.

10. The method of claim 9, wherein said polyphenolic compound is selected from tannic acid, ellagic acid and combinations thereof.

11. The method of claim 9, wherein said effective amount of said polyphenolic compound is from about 1 µg to about 10 µg.

12. The method of claim 9 further comprising administering a stimulator of elastogenesis selected from elastin-derived peptides, plant-derived peptides, bovine-derived peptides, manganese, iron, copper and combinations thereof.

13. The method of claim 12, wherein said polyphenolic compound and said stimulator of elastogenesis are administered simultaneously.

14. The method of claim 12, wherein said polyphenolic compound and said stimulator of elastogenesis are administered sequentially.

15. The method of claim 9, wherein said polyphenolic compound and said peptide are administered simultaneously.

16. The method of claim 9, wherein said polyphenolic compound and said peptide are administered sequentially.

* * * * *